(12) United States Patent
Belz et al.

(10) Patent No.: US 8,548,607 B1
(45) Date of Patent: Oct. 1, 2013

(54) AUTOMATION SYSTEM NETWORK MANAGEMENT, ARCHITECTURES, AND METHODS AND APPLICATIONS THEREOF

(75) Inventors: Robert Belz, Clear Spring, MD (US); Randy Clayton, Frederick, MD (US)

(73) Assignee: Autani Corp., Columbia, MD (US)

( * ) Notice: Subject to any disclaimer, the term of this patent is extended or adjusted under 35 U.S.C. 154(b) by 703 days.

(21) Appl. No.: 12/611,918

(22) Filed: Nov. 3, 2009

Related U.S. Application Data

(60) Provisional application No. 61/110,808, filed on Nov. 3, 2008.

(51) Int. Cl.
| | |
|---|---|
| G05B 19/18 | (2006.01) |
| G05B 21/00 | (2006.01) |
| G05B 13/00 | (2006.01) |
| G05B 15/02 | (2006.01) |
| G05B 19/042 | (2006.01) |
| G05B 19/05 | (2006.01) |
| F24F 11/00 | (2006.01) |

(52) U.S. Cl.
CPC .............. G05B 15/02 (2013.01); *G05B 19/042* (2013.01); *G05B 19/058* (2013.01); *F24F 11/0086* (2013.01)
USPC ................. 700/21; 700/11; 700/19; 700/276; 700/286

(58) Field of Classification Search
USPC .............. 700/11, 9, 12, 33, 286, 291, 21, 276
See application file for complete search history.

(56) References Cited

U.S. PATENT DOCUMENTS

| | | | | |
|---|---|---|---|---|
| 5,097,203 | A | * | 3/1992 | Haussmann et al. .......... 324/131 |
| 5,287,050 | A | * | 2/1994 | Kronenberg et al. ......... 318/696 |
| 5,696,695 | A | * | 12/1997 | Ehlers et al. .................. 700/286 |
| 6,751,562 | B1 | * | 6/2004 | Blackett et al. ............... 700/286 |
| 6,816,817 | B1 | * | 11/2004 | Retlich et al. ..................... 700/9 |
| 6,850,252 | B1 | * | 2/2005 | Hoffberg ....................... 715/716 |
| 6,901,316 | B1 | * | 5/2005 | Jensen et al. .................. 700/286 |
| 6,961,641 | B1 | * | 11/2005 | Forth et al. .................... 700/295 |
| 6,978,225 | B2 | * | 12/2005 | Retlich et al. ..................... 700/9 |

(Continued)

FOREIGN PATENT DOCUMENTS

| | | |
|---|---|---|
| JP | 05264290 A * | 10/1993 |
| WO | WO 2008092082 A2 * | 7/2008 |

OTHER PUBLICATIONS

Eckel, C.; Gaderer, G.; and Sauter, T., "Implementation Requirements for Web-Enabled Appliances—A Case Study", Sep. 2003, IEEE Conference on Emerging Technologies and Factory Automation, vol. 2, pp. 636-642.*

(Continued)

*Primary Examiner* — Mohammad Ali
*Assistant Examiner* — Kelvin Booker

(57) ABSTRACT

An automation system including a plurality of peripheral devices, each configured to perform at least one function relating to energy consumption in a facility and an automation controller in communication with the plurality of peripheral devices and providing for the control of the performance of the function by each device. An external network resource such as at least a virtual private network server is configured to enable communication with the automation controller. The automation controller is configured, such as by executing virtual private network software, to establish and maintain a secure data link with the virtual private network server and to enable oversight and/or control of the automation controller via the virtual private network server.

18 Claims, 17 Drawing Sheets

(56) References Cited

U.S. PATENT DOCUMENTS

| | | | |
|---|---|---|---|
| 7,127,328 B2* | 10/2006 | Ransom | 700/286 |
| 7,130,719 B2* | 10/2006 | Ehlers et al. | 700/276 |
| 7,136,709 B2* | 11/2006 | Arling et al. | 700/9 |
| 7,155,305 B2* | 12/2006 | Hayes et al. | 700/224 |
| 7,161,483 B2* | 1/2007 | Chung | 340/531 |
| 7,187,279 B2* | 3/2007 | Chung | 340/541 |
| 7,188,003 B2* | 3/2007 | Ransom et al. | 700/286 |
| 7,343,226 B2* | 3/2008 | Ehlers et al. | 700/291 |
| 7,379,778 B2* | 5/2008 | Hayes et al. | 700/90 |
| 7,409,303 B2* | 8/2008 | Yeo et al. | 702/60 |
| 7,539,533 B2* | 5/2009 | Tran | 600/509 |
| 7,558,622 B2* | 7/2009 | Tran | 600/509 |
| 7,574,283 B2* | 8/2009 | Wang et al. | 700/276 |
| 7,684,876 B2* | 3/2010 | Grgic | 700/19 |
| 7,734,380 B2* | 6/2010 | Ransom et al. | 700/286 |
| 7,761,910 B2* | 7/2010 | Ransom et al. | 700/286 |
| 7,797,204 B2* | 9/2010 | Balent | 705/28 |
| 7,804,280 B2* | 9/2010 | Deaver et al. | 323/210 |
| 7,865,252 B2* | 1/2011 | Clayton | 700/19 |
| 7,904,187 B2* | 3/2011 | Hoffberg et al. | 700/83 |
| 7,966,078 B2* | 6/2011 | Hoffberg et al. | 700/83 |
| 7,987,003 B2* | 7/2011 | Hoffberg et al. | 700/83 |
| 8,036,847 B2* | 10/2011 | Discenzo | 702/107 |
| 8,090,476 B2* | 1/2012 | Dawson et al. | 700/276 |
| 8,090,556 B2* | 1/2012 | Keefe et al. | 700/286 |
| 8,108,036 B2* | 1/2012 | Tran | 600/509 |
| 8,183,995 B2* | 5/2012 | Wang et al. | 340/539.1 |
| 8,260,628 B2* | 9/2012 | Lopez et al. | 705/1.1 |
| 8,323,188 B2* | 12/2012 | Tran | 600/300 |
| 8,328,718 B2* | 12/2012 | Tran | 600/300 |
| 2004/0107025 A1* | 6/2004 | Ransom et al. | 700/286 |
| 2004/0133314 A1* | 7/2004 | Ehlers et al. | 700/276 |
| 2004/0193329 A1* | 9/2004 | Ransom et al. | 700/286 |
| 2004/0225649 A1* | 11/2004 | Yeo et al. | 707/3 |
| 2005/0096753 A1* | 5/2005 | Arling et al. | 700/11 |
| 2005/0159823 A1* | 7/2005 | Hayes et al. | 700/19 |
| 2005/0222820 A1* | 10/2005 | Chung | 702/188 |
| 2005/0246408 A1* | 11/2005 | Chung | 709/200 |
| 2006/0069459 A1* | 3/2006 | Retlich | 700/9 |
| 2006/0259183 A1* | 11/2006 | Hayes et al. | 700/221 |
| 2006/0259184 A1* | 11/2006 | Hayes et al. | 700/221 |
| 2007/0043477 A1* | 2/2007 | Ehlers et al. | 700/276 |
| 2007/0043478 A1* | 2/2007 | Ehlers et al. | 700/276 |
| 2007/0053513 A1* | 3/2007 | Hoffberg | 380/201 |
| 2007/0242688 A1* | 10/2007 | McFarland | 370/445 |
| 2007/0273504 A1* | 11/2007 | Tran | 340/539.12 |
| 2008/0004904 A1* | 1/2008 | Tran | 705/2 |
| 2008/0183307 A1* | 7/2008 | Clayton et al. | 700/8 |
| 2008/0183316 A1* | 7/2008 | Clayton | 700/90 |
| 2008/0208361 A1* | 8/2008 | Grgic | 700/2 |
| 2008/0313006 A1* | 12/2008 | Witter et al. | 705/9 |
| 2009/0012650 A1* | 1/2009 | Wang et al. | 700/276 |
| 2009/0083167 A1* | 3/2009 | Subbloie | 700/286 |
| 2009/0227876 A1* | 9/2009 | Tran | 600/483 |
| 2009/0227877 A1* | 9/2009 | Tran | 600/483 |
| 2009/0240381 A1* | 9/2009 | Lane | 700/286 |
| 2009/0316671 A1* | 12/2009 | Rolf et al. | 370/338 |
| 2010/0094981 A1* | 4/2010 | Cordray et al. | 709/222 |
| 2010/0106332 A1* | 4/2010 | Chassin et al. | 700/278 |
| 2010/0106641 A1* | 4/2010 | Chassin et al. | 700/291 |
| 2010/0114387 A1* | 5/2010 | Chassin | 700/286 |
| 2010/0217837 A1* | 8/2010 | Ansari et al. | 709/218 |
| 2010/0235481 A1* | 9/2010 | Deutsch et al. | 709/222 |
| 2010/0241762 A1* | 9/2010 | Deutsch et al. | 709/245 |
| 2010/0324956 A1* | 12/2010 | Lopez et al. | 705/7 |
| 2011/0213472 A1* | 9/2011 | Clayton et al. | 700/11 |
| 2011/0246630 A1* | 10/2011 | Deutsch et al. | 709/222 |
| 2012/0095352 A1* | 4/2012 | Tran | 600/490 |
| 2012/0095357 A1* | 4/2012 | Tran | 600/509 |
| 2012/0330109 A1* | 12/2012 | Tran | 600/301 |
| 2013/0038468 A1* | 2/2013 | Wang et al. | 340/870.02 |
| 2013/0072807 A1* | 3/2013 | Tran | 600/485 |

OTHER PUBLICATIONS

Gungor, V.C.; and Lambert, F.C., "A Survey on Communication Networks for Electric System Automation", 2006, Computer Networks, vol. 50, No. 7, pp. 877-897.*

Platts, "HVAC: Building Automation Systems", 2005, McGraw-Hill Companies.*

Site Controls, "What the Smart Grid Means to Customers", 2009, Site Controls.*

* cited by examiner

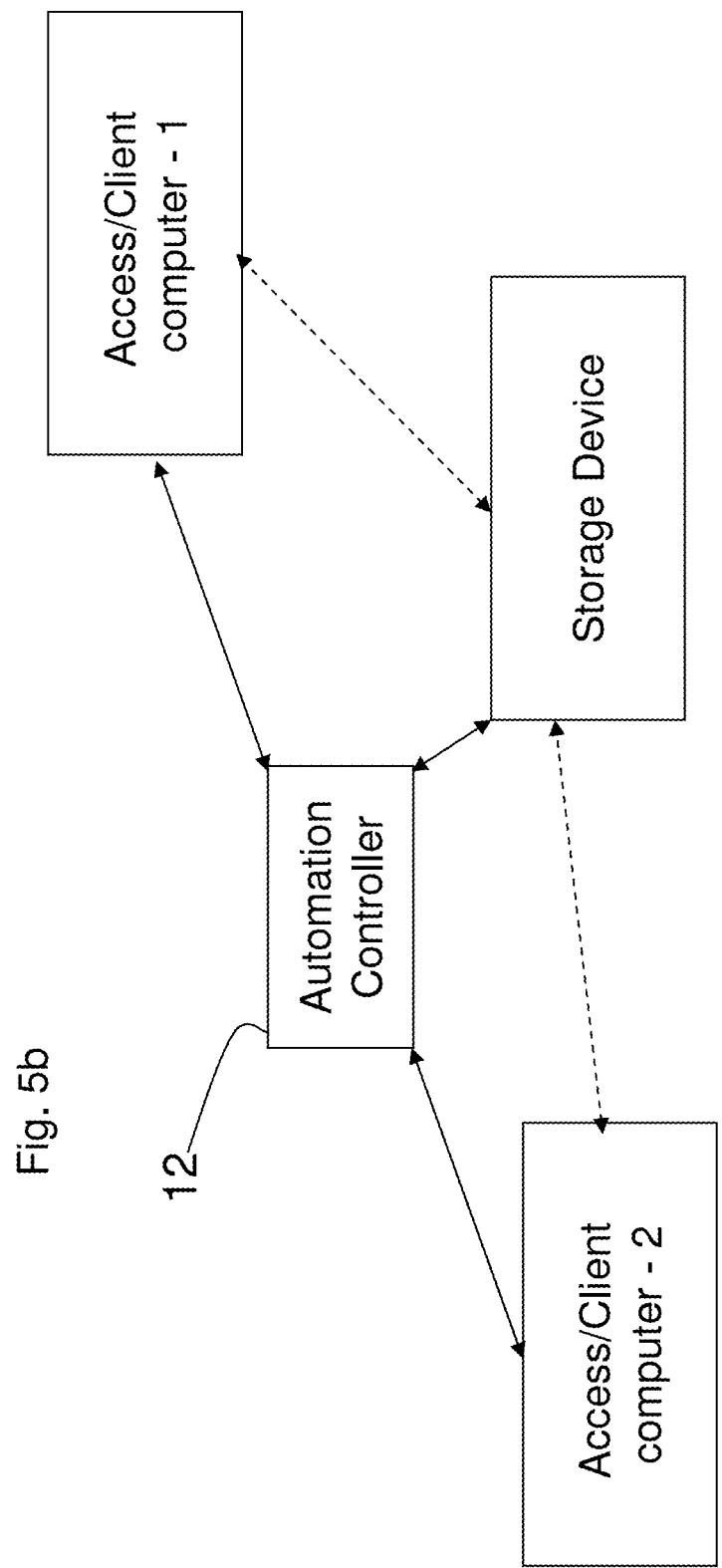

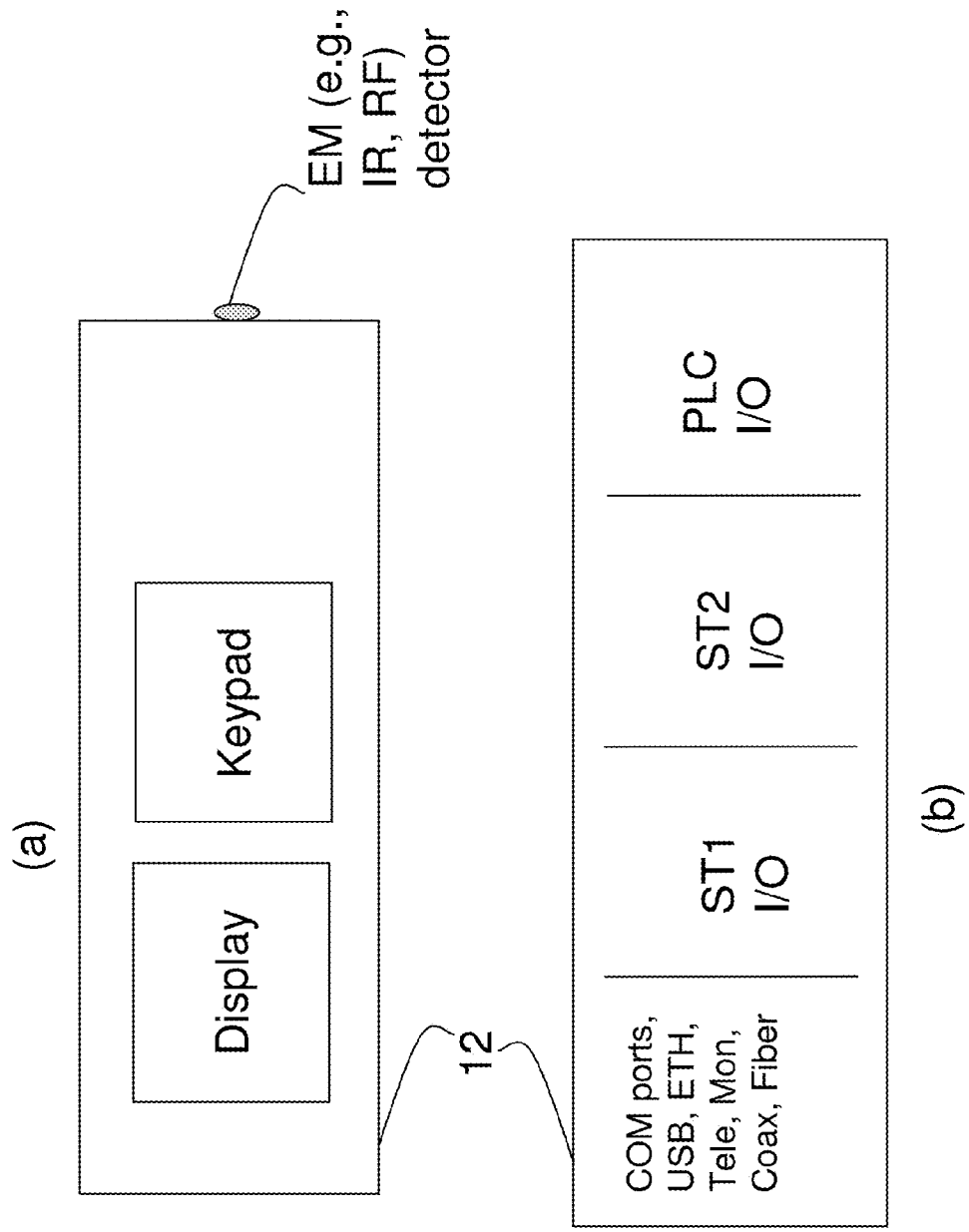

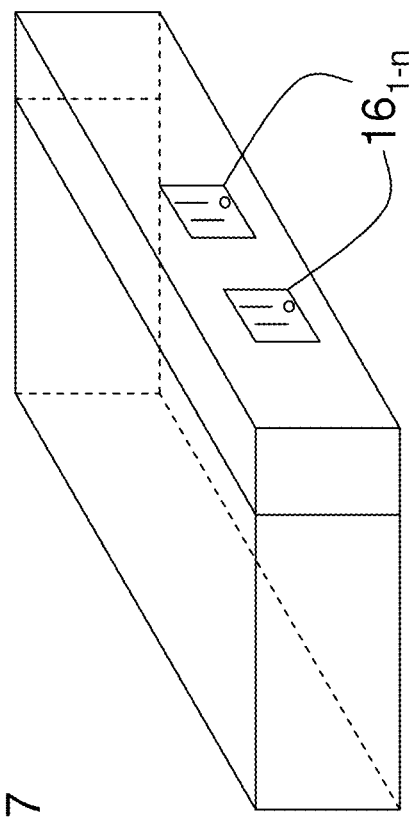

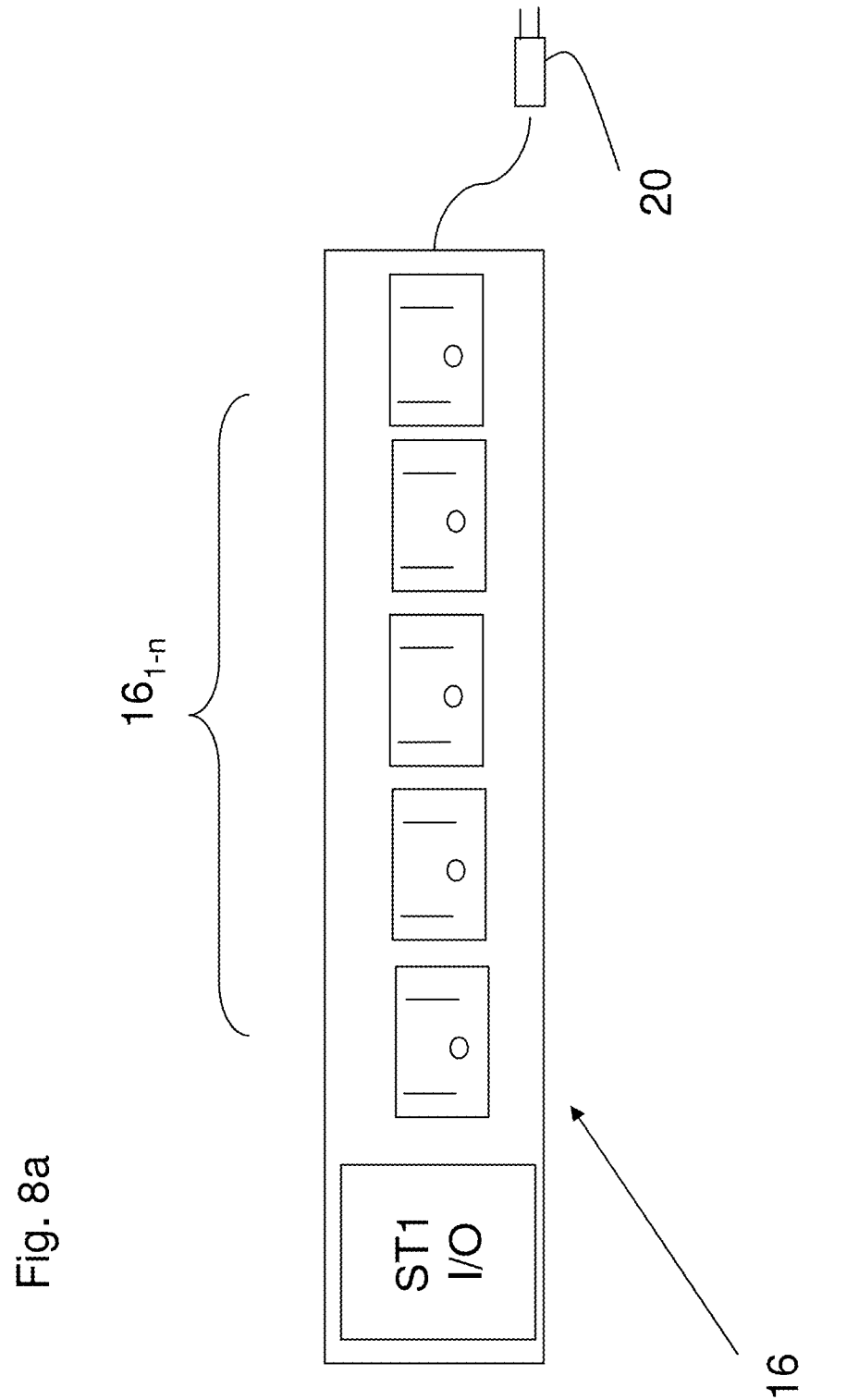

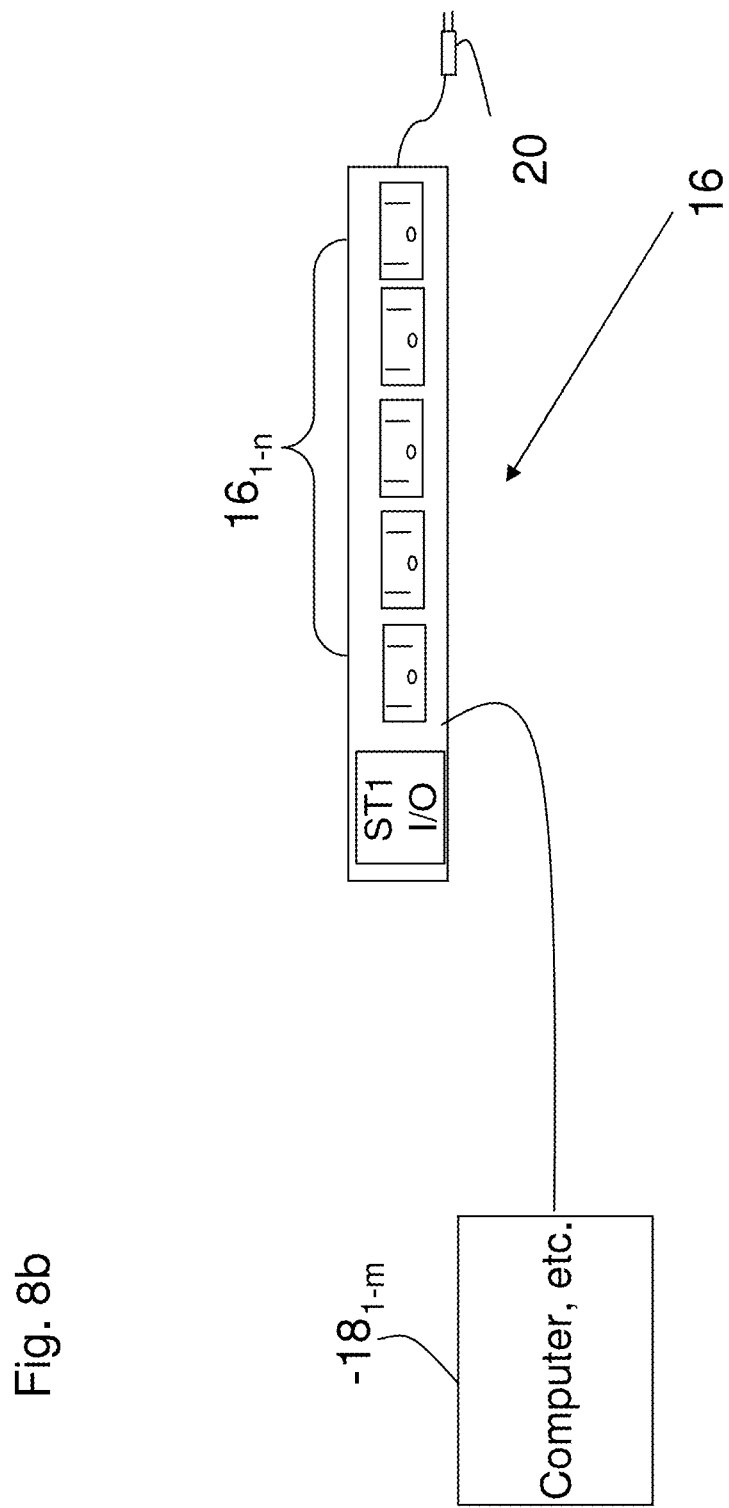

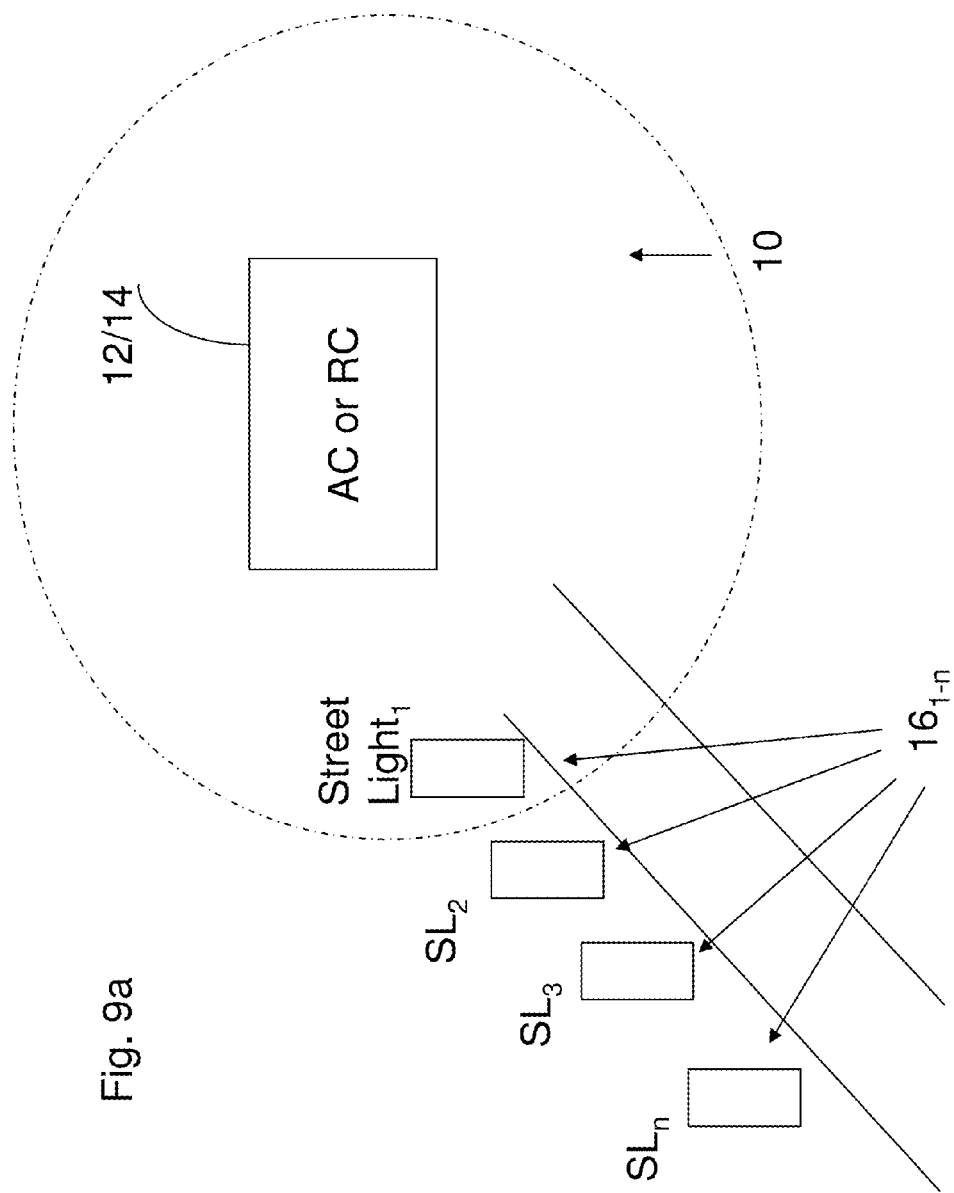

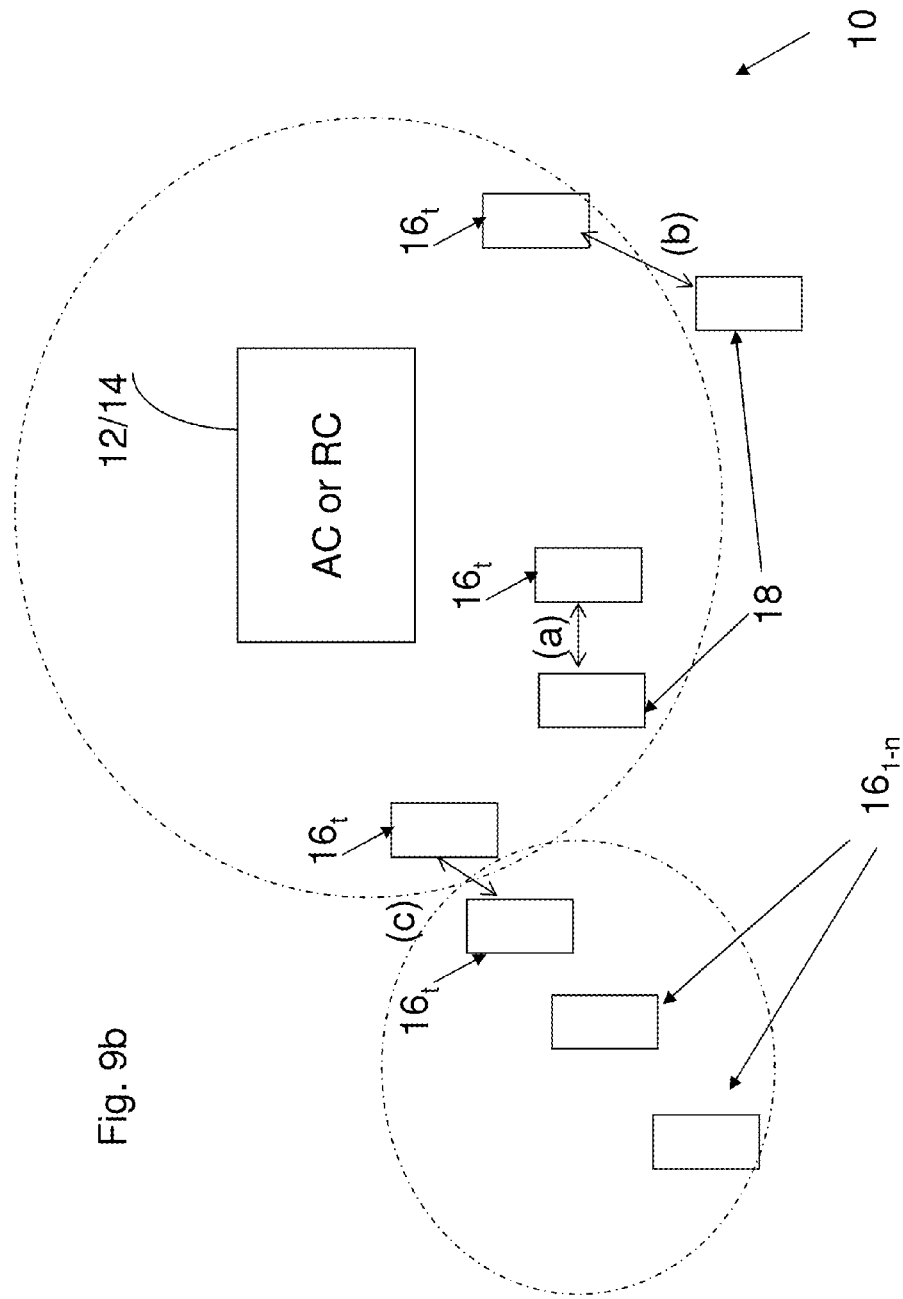

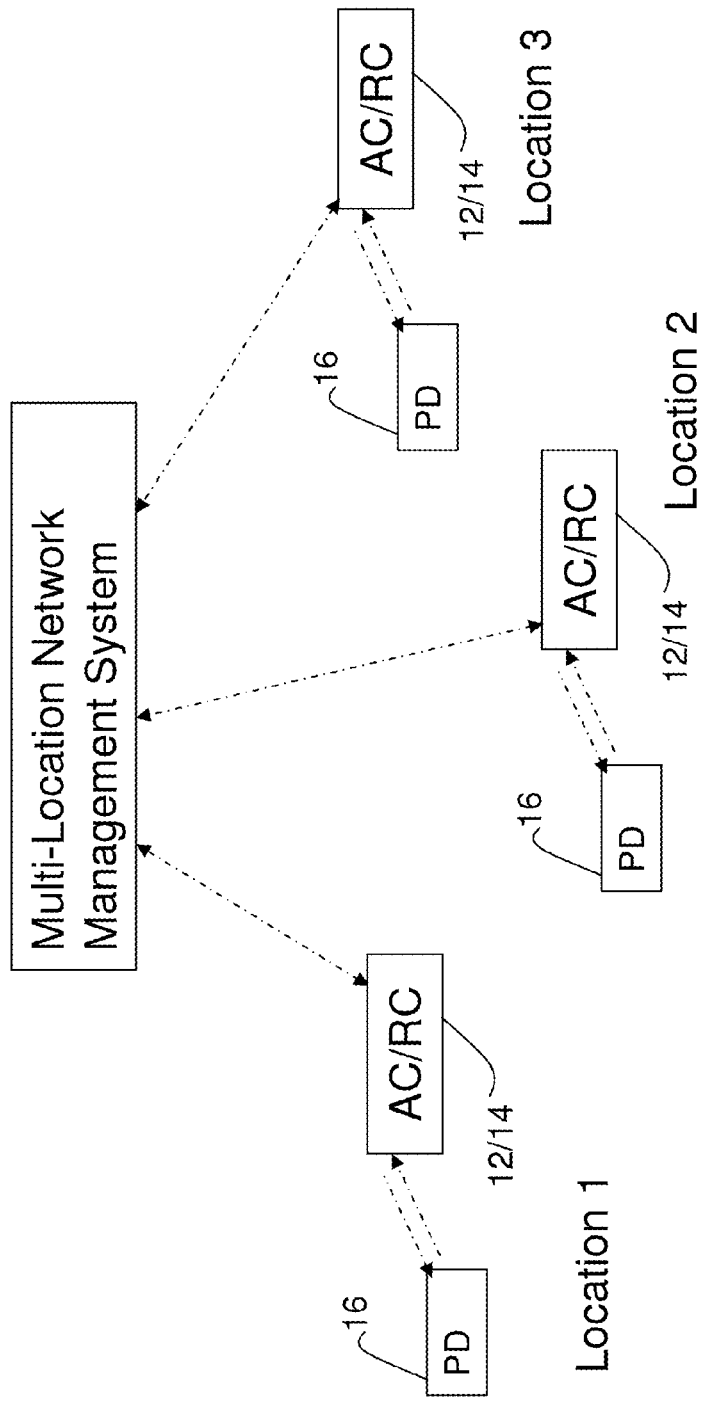

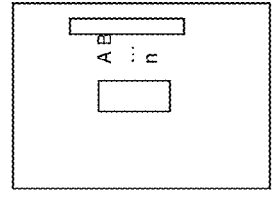
Fig 11
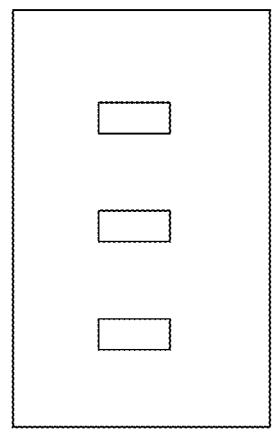
Fig 12
Fig 13
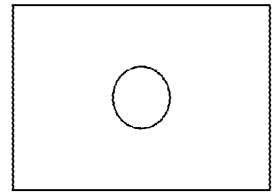
Fig 14
Front View
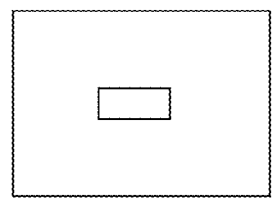
Side View
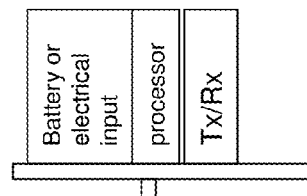
Fig 16
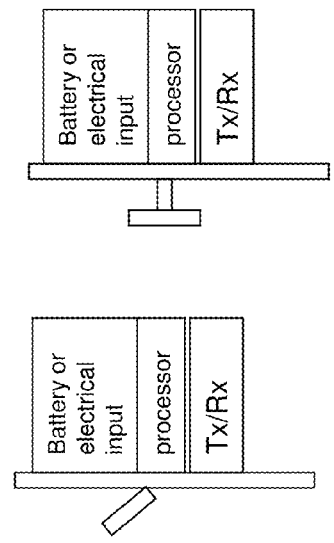
Fig 15

AUTOMATION SYSTEM NETWORK MANAGEMENT, ARCHITECTURES, AND METHODS AND APPLICATIONS THEREOF

CROSS-REFERENCE TO RELATED APPLICATIONS

This application claims the benefit of U.S. Provisional Patent Application No. 61/110,808 filed Nov. 3, 2008.

STATEMENT REGARDING FEDERALLY-SPONSORED RESEARCH AND DEVELOPMENT

Not Applicable.

FIELD OF THE INVENTION

The present invention is directed generally to automation systems and, more specifically, to automation system network management, architectures and methods to monitor and control conditions in and/or around buildings and the operation of energy systems.

BACKGROUND OF THE INVENTION

Automation of the work and leisure environment is a concept that has been long pursued. Despite the continued pursuit, widespread automation, particularly in the home, has not gone much beyond the use of timers, programmable thermostats, and universal remote controls for audio and video equipment.

In the home, higher levels of automation have been left to the domain of the hobbyist and high net worth individuals. A major reason being that home automation systems tend to be difficult to implement and maintain and/or extremely expensive relative to the utility and benefits of the system. Also, the solutions tend to be one size fits all, where the benefits associated with the systems are realized with large system deployments, irrespective of whether a person wants to automate an individual socket, a room, or an entire facility.

X10 has been the most widely implemented protocol in the home automation industry. X10 is a low-speed, unidirectional PowerLine Communication/Carrier (PLC) solution that uses a home electrical power wiring to communicate with various devices that control the various functions in the home, such as light switches, wall receptacles, thermostats, etc. Common criticisms of X10 are directed toward its reliability and robustness, as well as the level of user-friendliness. As such, these systems have been left to hobbyist and those people willing to pay professional contractors to install and/or maintain the systems. Other PLC protocols have been developed to address the criticisms of X10, which have enhanced performance and user experience, but have not substantially broadened the market for these products.

The high-end of the residential market has typically been addressed by comprehensive and expensive stand-alone systems, which often require the use of professional services firms to install and possibly maintain the system. These systems can be integrated with other systems, such as security and intercom systems, to defray the cost of system ownership. In addition to the price of the comprehensive system, the cost and inconvenience associated with providing an infrastructure to support these systems in existing structures has further constrained the market.

The emergence of wireless communication technology and digital media has reinvigorated the automation market, particularly the home market. New wireless protocols and standards are being developed and adopted to support wireless automation systems. The wireless systems are not constrained by power lines and do not require expensive wiring to build out a separate communication network or retrofit an existing structure.

Currently, there are two emerging protocols being introduced in the $1^{st}$ generation of standard wireless automation products, namely Zigbee and Z-Wave. Both protocols attempt to provide a wireless networking standard that supports low data rates, low power consumption, security and reliability. Zigbee is open standard based on IEEE 802.15.4, while Z-Wave is a proprietary standard developed by Zensys, Inc., the current sole source for the chips that implement the protocol.

Many of the high-end automation system vendors have developed media center systems for the distribution and control of audio and video signals throughout the structure, which also include some home automation functionality. The media center provides control over various automation devices deployed in the structure and typically be accessed locally by a computer or remotely via the Internet. A universal remote control is typically provided, which communicates with the media center, which, in turn, communicates with the audio, video, and automation devices.

Other products employ a gateway controller that is controlled from a remote network operations center ("NOC") via a network connection into the structure. The gateway controller controls devices in the structure based on information provided by the NOC and provide status information to the NOC. A remote control is provided to allow for control of the individual automation devices without having to reprogram the device through the NOC.

Outside the home in non-residential settings, whether it is for or non-profit, academic, governmental, social, etc., owners and tenants face challenges similar to those in the residential market. Non-residential energy consumers can employ highly sophisticated systems for controlling their heating, ventilation, and air conditioning ("HVAC"), as well as for access control and information technology. Otherwise, these consumers are also generally limited to the use of programmable thermostats and motion controlled lighting.

As such, most energy consumers have little visibility into their energy consumption patterns. The lack of visibility makes it difficult to modify or tailor consumption patterns to reduce the energy consumed or the cost of the energy being consumed. Furthermore, participation in utility based conservation programs, such as demand-response programs, is typically limited to those residential and non-residential facilities that can operate with periodic interruptions of their air conditioning systems.

In summary, existing systems in many instances do not provide a sufficiently compelling value proposition in terms of cost, ease of use, scalability, and overall utility to expand the market for these products. Improved automation solutions are required that overcome the various limitations associated with prior art solutions to enable high quality, cost effective, and scalable automation solutions for homes and businesses that can applied by the end users to their particular automation needs.

BRIEF SUMMARY OF THE INVENTION

The present invention provides, among other things, a scalable automation system that can be deployed as one or more independent systems at various times, which can later be consolidated and operated by a centralized automation controller either as independent systems or as one consolidated system. Unlike the prior art, the automation system of the present invention implements a hierarchical approach to the control platform that provides the end users with a wide range of implementation schemes allowing systems embodying the present invention to be tailored to the specific application and purpose of the user. The present invention can be implemented using various wireline communication platforms, e.g., powerline, twisted pair, coax, and fiber, and protocols, as well as wireless technologies employing Zigbee, Z-wave, Bluetooth, and/or other proprietary and/or open standard, e.g., IEEE 802.x, communication protocols.

In the present invention, automation components generally can be grouped into three different types, automation controller, remote controller, and peripheral, or controlled, device (or "peripherals"), which have different roles in the system, such as master or command (command a function be performed), slave or function (perform a function), and peer (master or slave depending on function). Notably, in the present invention, different component types can provide command functionality, as well as perform multiple roles at one time or different times, which provides significant benefits from an implementation standpoint, as will be discussed herein. Generally, the automation and remote controllers are peers from at least an interface perspective. The controllers are generally masters of the peripherals, making the peripherals slaves to the controllers, and the peripherals are generally peers to other peripherals.

The present invention provides for increased performance of automation systems through the implementation of networking layers, which enable the automation system to be partitioned into sub-network and a higher layer management network. The partitioning enable low latency control of peripheral devices and controllers in the sub-networks, while maintaining the integrated control of a single network through the higher level network.

In addition, the operation and control of automation systems can be enhanced through the use of secure data links, such as via one or more virtual private networks (VPN) to external network resources, such as a NOC, and in combination with the various controllers in the automation system. In various embodiments, the automation controller is configured with VPN software that enables the automation controller to establish a VPN with a remote VPN server that enables the owner/user/operator to have various levels of oversight and control of the various systems. For example, the VPN server can control the turn-up and configure the automation system with limited interaction, if so desired by the end user, as well as the maintenance of the system.

The present invention addresses limitations of the prior art as will become further apparent from the specification and drawings.

BRIEF DESCRIPTION OF THE SEVERAL VIEWS OF THE DRAWING

The accompanying drawings are included for the purpose of exemplary illustration of various aspects of the present invention, and not for purposes of limiting the invention, wherein:

FIGS. 6*a*-7 show embodiments of automation controller;
FIGS. 8*a*-9*b* show embodiments of peripheral devices;
FIGS. 10*a*-*b* show embodiments of a system including at least one mobile peripheral device;
FIGS. 11-16 show embodiments of LPRCs;

It will be appreciated that the implementations, features, etc. described with respect to embodiments in specific figures and variations thereof may be implemented by the skilled artisan with respect to other embodiments in other figures, unless expressly stated, or otherwise not possible.

DETAILED DESCRIPTION OF THE INVENTION

Figure 1:
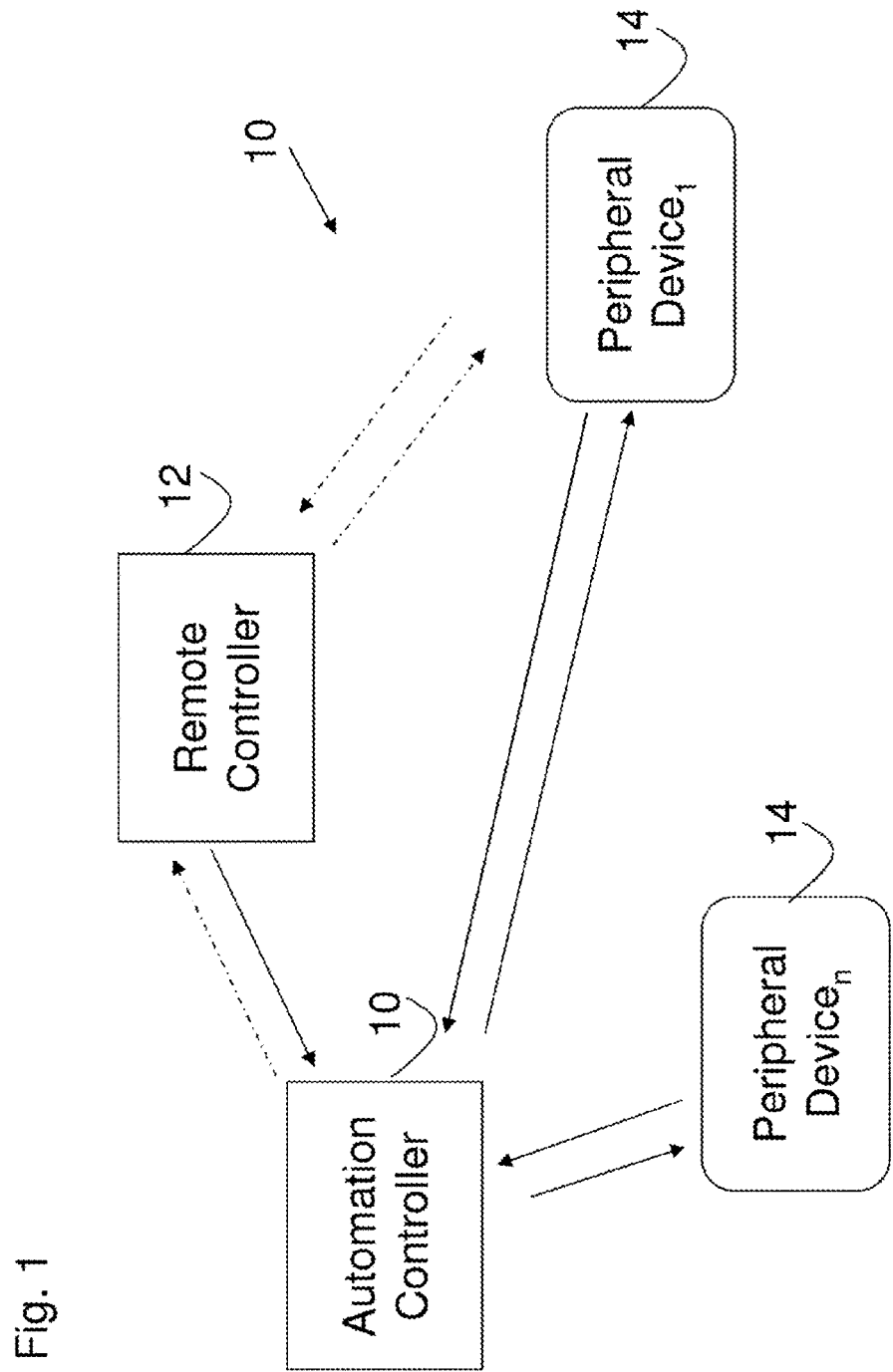
FIGS. 1-5*b* show embodiments of automation systems.

FIG. 1 depicts an automation system 10 embodiment of the present invention. The system 10 includes various components, such as an automation controller 12, a remote controller 14, and one or more peripheral devices $16_{1-n}$. In this embodiment, the automation controller 12 has two way communications with the peripheral device 16 (as shown by the solid arrows). It also has at least one way communication with the remote controller 14, and, optionally two way communications with the remote controller 14 (as indicated by the dashed arrows). In addition, the remote controller 14 can have optional one or two way communications with one or more of the peripheral devices $16_{1-n}$.

Communication between the automation controller 12 and the peripheral devices 16 can be wired and/or wireless depending upon the particular implementation. Wired communication can make use of the power lines, local area networks, or direct links between communication ports, such as USB, RS-232 and 485, etc. Wireless communications can employ one or more wireless technologies, such as Zigbee, Z-wave, Bluetooth, and/or other proprietary and/or open standard, e.g., IEEE 802.x, communication protocols transmitting signals in the infrared and/or radio frequency spectrum. As mentioned above, Zigbee and Z-wave are protocols that have been developed specifically for applications, such as automation, where some of the devices used in the system, such as those operating on battery power, may require low power, reliable, non-line of sight communication.

In embodiments such as FIG. 1, the automation controller 12 may serve as a peer or slave to the remote controller 14 depending upon the desired level of functionality and communication between the controllers. For example, when one way communication is provided from the remote controller 14, the automation controller 12 will act only as a slave performing an operation in response to a command/input from the remote controller 14. In embodiments providing for two way communication, the controllers may serve as peers or as a master and slave depending upon the configuration of the system 10. For example, if the only communication from the automation controller 12 to the remote controller 14 is to send information requested by remote controller 14, then the automation controller 12 will operate as a slave to the command/input sent by the user via the remote controller 14. Conversely, if the automation controller 12 can request/command certain actions be taken by the remote controller 14, such as report a status, then the controllers will most likely be operating in a peer relationship.

Embodiments based on FIG. 1 may include one or two way communication between the remote controller 14 and one or more of the peripheral devices 16. The remote to peripheral communication can provide primary, secondary, or alternate communications. For example, the remote controller 14 may be configured merely to serve as a repeater, and thus a peer to peripheral devices 16, for communications between the automation controller 12 and the peripheral devices 16. The remote controller 14 may send a command to the peripheral device 16 that is redundant of command sent by the automation controller 12.

Also, the remote controller 14 may send the only command to the peripheral device 16. In this instance, the automation controller 12 may be configured to receive this command from the remote controller 14 or the remote controller 14 may send a different command, such as a generic change of state command to the automation controller 12. Upon receipt of a command directed to a peripheral device by the remote controller 14, the automation controller 12 could 1) query the peripheral devices 16 immediately or at a predetermined time to determine its operational state or 2) await a communication from the peripheral devices 16 directly, and/or indirectly via the remote controller 14, indicating their state.

Figure 2:
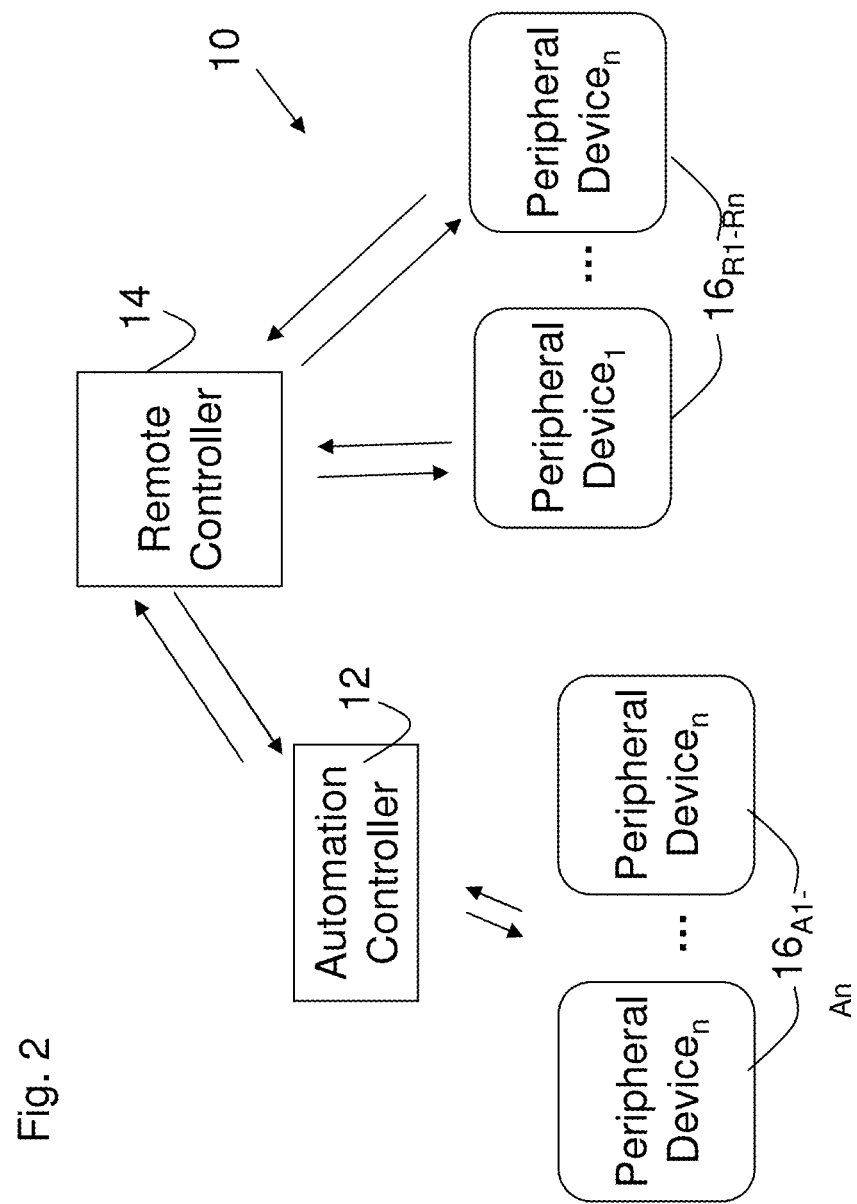

FIG. 2 shows embodiments of the system 10 including the automation controller 12, at least one remote controller 14, a first group of one or more peripheral devices $16_{a1\text{-}an}$ and a second group of one or more peripheral devices $16_{r1\text{-}rn}$. In these embodiments, the automation controller 12 communicates directly with the remote controller 14 and the first group of one or more peripheral devices $16_{a1\text{-}an}$. However, it does not communicate directly, and perhaps not at all, with the second group of one or more peripheral devices $16_{r1\text{-}rn}$.

In FIG. 2 embodiments, communication and control of the second group of one or more peripheral devices $16_{r1\text{-}rn}$ is performed via the remote controller 14. In various embodiments, the automation controller 12 will not associate or monitor some or the entire second group of peripheral devices $16_{r1\text{-}rn}$. In other embodiments, the automation controller 12 will monitor some or the entire second group of peripheral devices $16_{r1\text{-}rn}$, as the second group provides status information to the remote controller 14. In other embodiments, the automation controller 12 will indirectly control some or the entire second group of peripheral devices $16_{r1\text{-}rn}$, via commands sent to the remote controller 14. The automation controller 12 may also monitor the second group of peripheral devices $16_{r1\text{-}rn}$, via the remote controller 14, which can serve as a repeater or to provide additional information along with the monitoring information to the automation controller 12.

The architecture provided in FIG. 2 provides additional flexibility in tailoring the system 10 for a specific application. For example, the second group of peripheral devices $16_{r1\text{-}rn}$, may be implemented using a different communication scheme, which is only implemented on the remote controller 14. For example, in various embodiments, the remote controller 14 may be capable of communicating using both IR and RF frequencies, whereas the automation controller 12 may only be implemented using RF frequencies, or different protocols may be implemented on the remote controller 14 and the automation controller 12. In those instances where the communication protocol between the remote controller 14 and the second group of peripheral devices $16_{r1\text{-}rn}$, differs from the communication protocols implemented on the automation controller 12, then the remote controller 14 may serve to translate the information being provided from the second group of peripheral devices $16_{r1\text{-}rn}$ to the automation controller 12.

Figure 3:
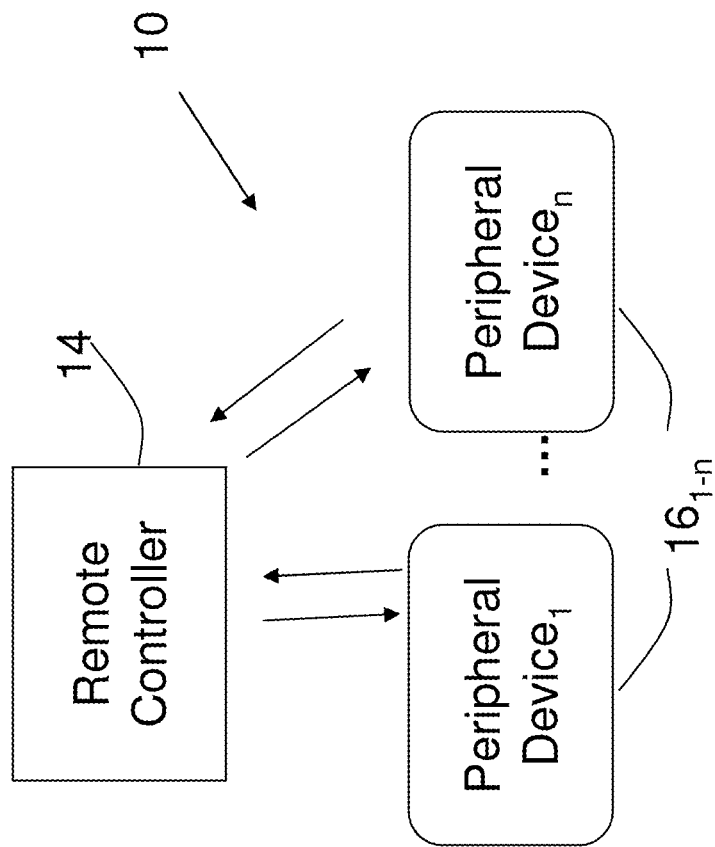

FIG. 3 shows embodiments of the present invention, in which the remote controller 14 is used to control one or more peripheral devices $16_{1\text{-}n}$, without an automation controller 12 in the system 10. The remote controller 14 can be used to implement various functions on the peripheral devices 16 depending upon the functionality imparted to the remote controller 14. For example, the processing power, storage capability, user interface, input/output capability, etc. can be tailored to control various numbers of peripheral devices 16 and impart various levels of functionality to the system 10 in the absence of the automation controller 12.

In various embodiments, the remote controller 14 is configured to communicate directly with the peripheral devices 16 using a suitable protocol, such as Zigbee, Z-Wave, etc., in a first state to send and receive information regarding the function of the peripheral device 16. The remote controller 14 is further configured to operate in a second state in the presence of an associated automation controller 12, where the remote controller 14 communicates directly with the automation controller 12, instead of the peripheral devices 16. If the automation controller 12 becomes unavailable, either because it is removed from the system 10, either physically or via software, or is not working properly, the remote controller 14 will recognize that the automation controller 12 is no longer present, or more generally unassociated with the remote controller 14, and operate in the first state.

In practice, the system 10 may be in operation without an automation controller 12 using the remote controller 14 to control a plurality of peripheral devices 16. The remote controller 14 recognizes that there is not an associated automation controller 12, so it operates in the first state, directly communicating with and controlling the peripheral devices 16. When the end user of the system 10 introduces an automation controller 12 into system 10, the remote controller 14 recognizes that the automation controller 12 and operates in a second state communicating with the automation controller 12, instead of directly with the peripheral devices 16. As discussed with respect to FIG. 2, the system 10 can be configured so that the remote controller 14 continues to communicate directly with the second group of peripheral devices 16, while communicating via the automation controller 12 with the first group of peripheral devices 16.

The ability of the remote controller 14 to move between the first and second states can be manually and/or automatically implemented. A hardware switch or software defined key can be used to toggle manually between the first and second states.

In addition, it may be desirable to keep remote controllers 14 unassociated with automation controller 12 that are detected. For example, in an apartment complex or other space where multiple users are in close proximity, the automation controller 12, as well as other remote controllers 14 and peripheral devices 16 that are within the system 10 operating range may not belong to the end user. In addition, the end user may want to partition a structure to include separate system 10, which may or may not report to a single system for oversight and control.

The association of an automation controller 12 that is introduced into an existing system 10 being controlled by the remote controller 14, in the absence of an automation controller 12, can be performed in a number of ways. For example, the automation controller 12 can scan its coverage area and develop a list of peripheral devices 16 and remote controllers 14 that can be associated with the newly introduced automation controller 12. Also, the remote controller 14 can transfer system information to the automation controller 12, such as a listing of currently associated peripheral devices 16, current settings, and activity schedules.

In these embodiments, the automation controller 12 and the remote controller 14 will continue to operate in a peer relationship, even though the remote controller 14 may not be communicating directly with the peripheral devices 16. The peer to peer communication would be used by the automation controller 12 to update the remote controller 14 with the latest settings and other information for the peripheral devices 16 that the remote controller 14 would communicate with directly and control, if the automation controller 12 became unassociated with the system 10 during operation.

In various embodiments, where the remote controller 14 may or may not be configured to control the system 10 in the absence of the automation controller 12, peer to peer communication between the remote controller 14 and the automation controller 12 may be implemented to enable additional system functionality. For example, persistent storage may be included in the remote controller 14 and the automation controller 12 can be configured to send information concerning the setup and/or operation of the peripheral devices 16 and the automation controller 12 to the remote controller 14 as a data back-up, in the event that the automation controller 12 experiences an outage where data is lost. In addition, the automation controller 12 could be used to change the peripheral devices 16 that will be controlled by the remote controller 14, if the automation controller 12 becomes unassociated with the system 10.

In the some of the above embodiments and others, the remote controller 14 acts as an autonomous device, i.e., without a user inputting information. In these embodiments, it may be desirable to have the remote controller 14 operate in a sleep mode, e.g., with display lights off, etc., and/or include a manual control, such as a switch, to switch the remote controller 14 to a lower power operational state. The sleep/low power mode will extend the battery life. In some embodiments, a holder, or cradle, can be provided for the remote controller 14 that can be used to provide various levels of functionality. For example, the holder may include a power outlet to charge a rechargeable battery. It also may include a communication link for direct communication with the automation controller 12, other network devices, or an external network. The communication link could allow for the download of configuration files for controlling peripheral devices 16 and secondary devices (described below), software updates, etc.

Figure 4:
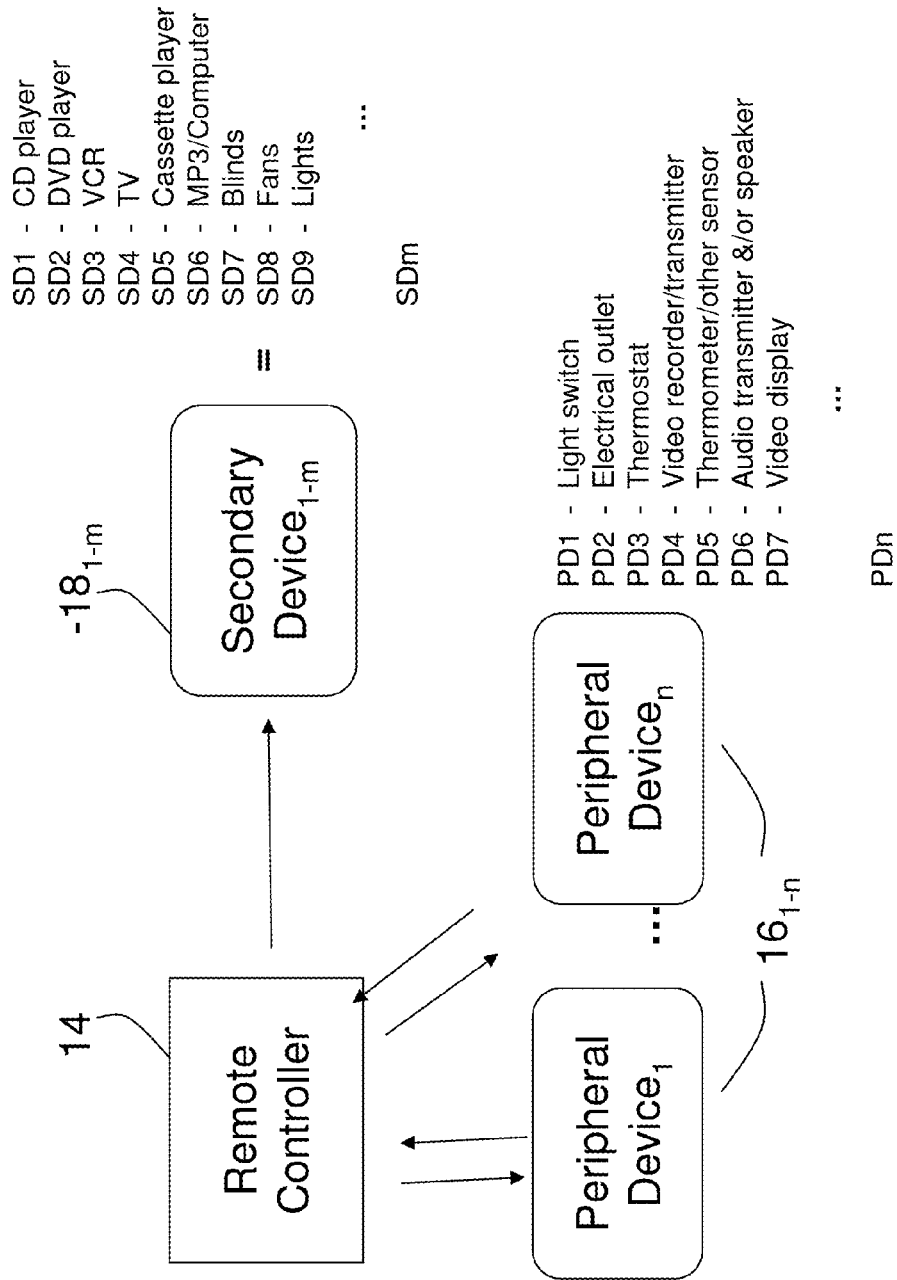

FIG. 4 depicts embodiments of the remote controller 14, in which the remote controller 14 is used to communicate to the peripheral devices 16 via a first signal type, such as Zigbee, and to one or more secondary peripheral devices 18 via a second signal type, such as proprietary Infrared (IR) and/or RF signals. The embodiments enable the remote controller 14 also to serve as a traditional "universal remote" for typical secondary peripheral devices 18, such as audio and video analog and digital players and recorders (e.g., CD, DVD, VCR, cassette, etc.), televisions/monitors, computers and peripherals, such as MP3 players, blinds, fans, and lights.

Figure 5A:
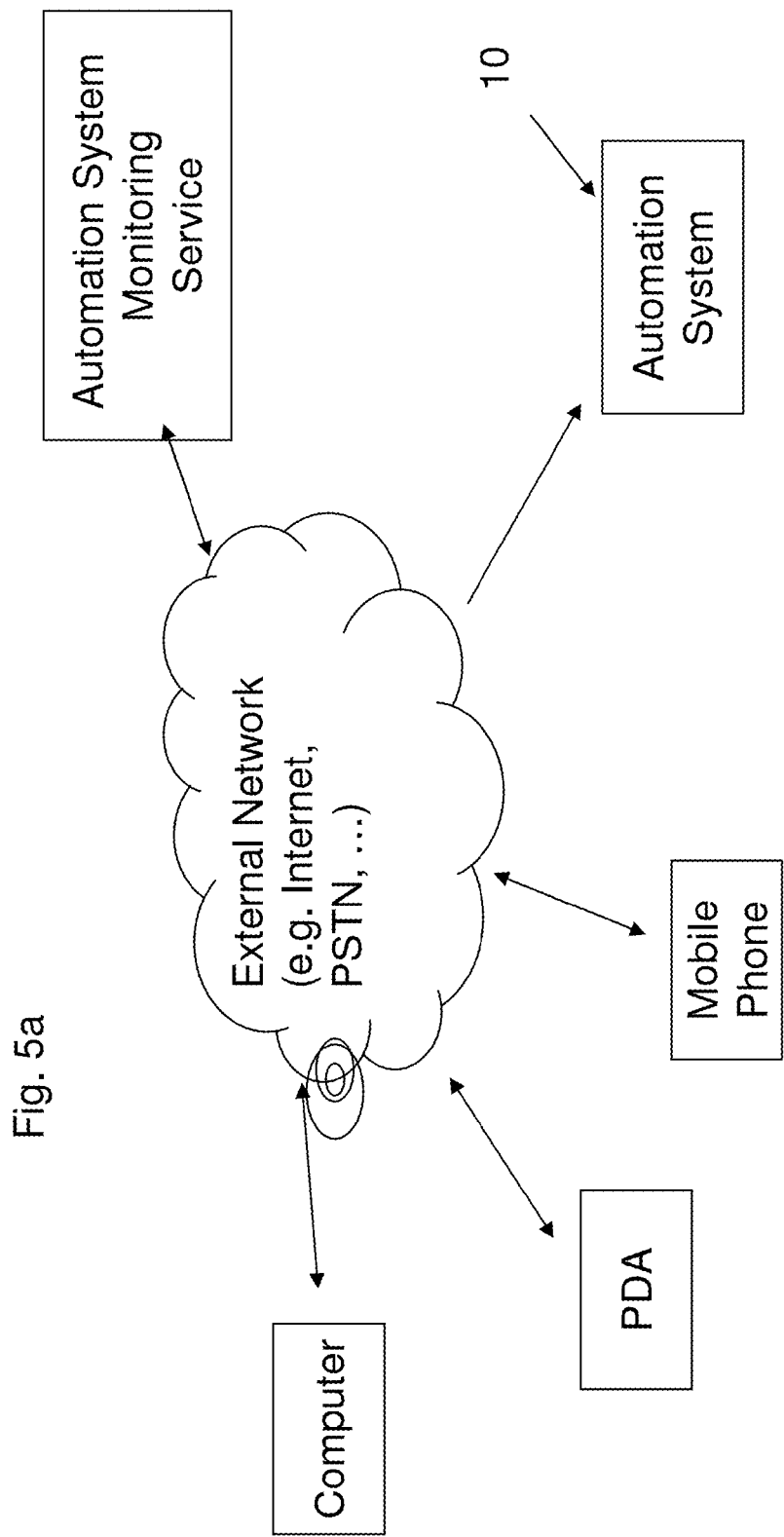

FIG. 5*a* shows system 10 embodiments that include connectivity to various input, output, and monitoring devices ("input/output devices") via an external network, such as the Internet, PSTN, etc. Access to the system 10 can be enabled from a variety of devices, such as computers, mobile and fixed phone lines, personal digital assistants (PDA), etc., as well as from third party service provider networks for system monitoring and control. For example, a computer can communicate directly with the automation controller 12 or via one or more networks including personal, local, metro, and wide area, public and private, intranet and internet networks. Access via the external network provides the end user with the capability to monitor and configure the system 10 remotely. For example, it may be desirable to change the temperature in the house before returning home, or to receive a text message letting you know that some event, such as a door opening, a smoke or CO detector sounding, tagged item/mobile device moving across a threshold, etc.

As shown in FIG. 5*b*, the automation controller 12 also can be deployed in client-server architecture, in which one or more computers, acting as clients, provide data entry and access to the controller 12. The client can also interact with storage devices supporting data storage for the system 10 either directly or via the automation controller 12. As previously described, the automation controller 12 functionality can be distributed among a number of automation controllers 12 with oversight from a master controller 12, which may further include client computers for data entry and access. Additional devices also can be employed to provide additional functionality or robustness to the system. For example, storage devices could be employed to off-load data collected by the automation controller 12. Access to the storage devices could be achieved via the automation controller 12 and/or directly by another computer, which can provide analysis capability off-line from the automation controller 12.

In various embodiments in which data is stored in a device external to the automation controller 12, it may be desirable to enable various software applications on the client computers to enable analysis and planning activities to be performed without burdening the automation controller 12. For example, client computers can run planning and analysis software tools that enable the user view detailed and consolidated usage information. Planning activities, such as evaluating the impact of varying operational hours or replacing various electrical systems can be investigated using historical data from the system 10.

FIGS. 6*a* and 6*b* depict various embodiments of the automation controller 12. In many system 10 embodiments, the automation controller 12 will provide system oversight, coordination, and control of the peripheral devices 16 and the remote controller 14. Access to the automation controller 12 can be provided internally by the controller and/or external to the controller. In various embodiments, the automation controller 12 may be fully autonomous with data entry and access capabilities provided directly on it. In other embodiments, data entry and access to the automation controller 12 may be completely external.

As shown in FIG. 6*a*, the automation controller 12 may include a keypad and/or a visual display to enter and view information. In various embodiments, a touch screen interface may be included to combine the data entry and viewing functionality. In other embodiments the data entry and viewing functionality will be provided outside of the automation controller 12 via a monitor and/or television screen with data entry via the remote controller 14 or support a display and keypad similar to a stand-alone computer.

The front of the automation controller 12 may also include an IR detector for those embodiments that support receiving IR signals. In those embodiments, the IR transmission capability of the remote controller 14 can be employed to control the automation controller 12, instead of using the RF transmission link. Also, the automation controller 12 can support the use of a more traditional remote that transmits only using IR signals.

FIG. 6*b* depicts an exemplary back view of the automation controller 12. It will generally include a variety of communication ports and transmitters and receivers for the various transmission protocols that are supported. For example, telephone, Ethernet, coax, and/or fiber connections can be provided. USB, RS-232 and 485 and other access ports and monitor connections. Transmitters and receivers for the various wireless transmission protocols are also included. For example, a Zigbee or Z-wave transmitter and receiver can support a first signal type ($ST_1$) and one or more 802.x transmitters and receivers can support networking via a second signal type ($ST_2$). In various embodiments, the automation controller 12 will also include an interface to support power line communications with peripheral devices 16 that communicate via power line protocols, such as X10.

In addition to the input/output and networking connections and associated hardware and software interfaces, the automation controller 12 will generally include one or more storage devices, as well as one or more processors, depending upon the particular capability being implemented on a particular automation controller 12 embodiment. In general, the automation controller 12 will provide most monitoring, coordination, control, and record keeping functions for the system 10. The desired system size and capabilities will drive the level of functionality in the embodied in the automation controller 12.

The automation controller 12 will typically connect to external power. The automation controller 12 may also include a battery back-up, in case of an external power failure, depending upon the level of reliability desired. While the automation controller 12 could be operated on battery power only, the functionality of the controller 12 generally warrants a continuously available (excepting failures) power source.

While varying levels of functionality can be embodied in the remote controller 14, in many embodiments, the full features and functionality of the system 10 are typically accessible and controllable via the automation controller 12. The automation controller 12 will generally provide menu-driven access to control the peripheral devices 16. The capability to check, change and schedule a change in status and/or settings for the peripheral devices 16 is generally provided. The automation controller 12 generally stores the system inventory and settings and may also be configured to store that information externally, such as in a computer or mass storage device, or at an off-site network operations center. The backup of system information can be performed manually or automatically.

Discovery and association of automation controllers 12, remote controllers 14 and peripheral devices 16 with the automation controller 12 and/or remote controller 14 can be a manual, automatic, or semi-automatic process. In some embodiments, the automation controller 12 will scan its operational range to discover various system components including other automation controllers 12, remote controllers 14 and peripheral devices 16 with which it can be associated. The automation controller 12 can update its potential inventory list each time it detects a new components.

As part of the discovery process, the automation controller 12 can employ various discovery methods. For example, it can "ping" all the components in its transmission range to send discovery information to the automation controller 12 to ensure a timely and complete inventory is established. The automation controller 12 can also "listen" for signals from components in its reception range, which can be compared to its inventory lists derived from pinging or otherwise. The automation controller 12 can be configured to continue discovery via pinging, listening, or otherwise until a consistent inventory list is produced. Alternatively, it can provide an inventory list of components that can be confined via multiple discovery methods, which can be used to define its operational range. It can also identify components that were discovered using one method, but not confined via another method. For example, a component that the automation controller 12 discovers by listening, but it does not responds to the ping signal sent by the automation controller 12. In this example, the component may be within the reception range of the automation controller 12, but not the transmission range for one or more reasons, such as shielding, partial component failure, etc.

Association of the peripheral devices 16 and remote controllers 14 with the automation controller 12 can be performed automatically as part of the inventory process. However, it is often times more desirable, even though it is more work, to have the association process be separate from inventory to ensure that only desired associations are made.

The association procedure for components with the system 10 can involve interaction between the component and the controller as part of the procedure and/or the user can associate the component. The procedure may be limited to adding a component identifier/address to a system database or may be more involved, such as configuring the component to assume particular operational states and/or roles in the network following the association.

In some instances, it may be desirable to require interaction between the component and the controller to minimize the chances of an improper association. For example, the peripheral devices 16 and remote controllers 14 may have an associate button, switch, key, etc., that must be activated during association. Alternatively, each device may have an association code or device identifier, such as a MAC address, that is entered via the automation controller 12 and/or the remote controller 14 as part of the association process without requiring communication between the controller and the component. The component will then respond to any controller that uses the proper address.

In various embodiments, a remote controller 14 can be used to initiate and/or perform the association or commissioning process using line of sight communications, such IR, in lieu of or combination with non-line of sight communications, e.g., Zigbee. The use of line of sight communication significantly reduces the probability of a peripheral device or other component being associated with a wrong network in deployment scenarios where systems have overlapping operational ranges, such as in multi-tenant facilities, and does not require physical interaction with the components.

In an exemplary association process, the remote controller 14 is configured to provide a line of sight signal, i.e., an IR signal, to the peripheral device 16 placing it in an association mode, where it will become associated with the automation controller 12 and/or with the remote controller 14. In some instances, the peripheral device 16 will remain in an association state until an automation controller 12 and/or remote controller 14 detects its presence and completes the association process. The detection of the peripheral device 16 by the automation controller 12 can be initiated by the remote controller 14 and/or peripheral device 16. For example, the remote controller 14 can be configured to send an association signal to the automation controller 12, in addition to the peripheral device 16. In this example, it may be desirable for the remote controller 14 to send a code/key to the automation controller 12 and peripheral devices 16 that is used in the association process to prevent the inadvertent initiation of the association process with another automation controller 12 within the range. If the association process is not initiated on the automation controller 12 by the remote controller 14, it may be desirable for the remote controller 14 to provide a code/key to the peripheral device 16 for identification in the association process, when it is detected by the automation controller 12.

In embodiments without a remote controller 14, the automation controller 12 can be configured to associate only with peripheral devices 16 and/or other automation controllers 12 for which a physical address, such as a MAC address, or code/key has been entered into the automation controller 12. The automation controller 12 can also be configured to associate with new components when it is in an association mode as discussed above, as opposed to trying to associate automatically with any component it detects during operation.

In some embodiments, it may be desirable to associate a peripheral device with an automation controller 12, when the peripheral device is not present within the communication range of the automation controller 12. For example, it may be desirable to associate a peripheral device with multiple automation controllers 12 within one or different systems 10 that have non-overlapping ranges of operation. One such embodiment of non-overlapping ranges is described below with respect to geographically diverse systems that share peripheral devices 16. The association between peripheral devices 16 and automation controllers 12, whether present in the range or not, can be performed by either or both devices 16 and controllers, using identifiers and signaling prompts, as may be appropriate.

Peripheral devices 16 in the present invention are generally implemented in a function role communicating directly with remote controllers 14 and/or automation controllers 12 depending upon the system configuration and responding to their commands to perform a function, which may include one or more steps, process, and/or actions. Common peripheral devices 16 include electrical wall and device receptacles and jacks, on/off, contact, and dimmer switches, visual (e.g., motion), audio, material (smoke, humidity, CO, radiation, etc.), electromagnetic wave (RF, IR, UV, visible light, etc.), shock, and thermal sensors, thermostats, video equipment (e.g., cameras, monitors), audio equipment (e.g., microphones, speakers), blinds, fans, communication equipment used to provide services, such as plain old telephone service (POTS), voice over Internet Protocol (VoIP), video, audio, and data, etc.

The peripheral devices 16 can also be used to obtain data from other devices for evaluation, referred to herein as monitoring peripheral devices 16. For example, a sensor or other peripheral device 16 can configured to monitor signals output by a piece of equipment or other device and send the signals along with the notification of the signaling event. The signals can be error codes or other performance attributes in various forms, such as visual (flashing lights), audible (beeps), and/or electrical signals that are detected by the devices 16 and forwarded by the system 10 to the relevant parties, if desired. For example, light pattern changes on LEDs (flashing, color, etc.) on computer equipment could be converted to an error code for evaluation or the audible signal from a smoke detector could be evaluated to distinguish low battery alerts from actual smoke detection.

Data from monitoring peripheral devices 16 can be used as primary data or as data to corroborate data received from other peripheral devices 16 within the system 10. For example, when a smoke detector is embodied as a peripheral device 16 in the system 10, the system 10 can be configured such that the automation controller 12 receives a smoke detected alarm from the smoke detector peripheral device 16 and a corroborating alarm from an audible monitor peripheral device 16 that detected the smoke detector audible alarm.

The peripheral devices 16 can operate on external and/or battery power depending upon the requirements of a particular device and the accessibility of external power. For example, electrical receptacles may not be required to transmit and receive information frequently, so they could be operated on battery power. However, electrical receptacles are connected in an external power circuit, so those devices will generally be operated using external power, because it is available. Similarly, peripheral devices 16 that are communicating with the automation controller 12 via a powerline communication protocol will be configured generally to use external power as those devices will be connected by the external power lines. If the function of the peripheral devices 16 is something that should remain operational, even when there is an external power outage, then it may be desirable to provide battery power as the primary or secondary power source to the device.

The peripheral devices 16 can be controlled individually by the controllers or in groups to create "scenes" or to place a structure in a particular operational state, such as set the air and water temperatures, disabling/enabling the door alarms, turning on/off computer equipment and other electrical devices, and unlocking/locking the garage and other doors when a business opens/closes or a person leaves/returns to a residence.

In some embodiments, such as depicted in FIG. 7, it is desirable to include one or more peripheral devices 16 packaged along with or proximate to the automation controller 12. The close proximity of the peripheral devices 16 to the automation controller 12 allows for a direct wired connection in lieu of, or in addition to, the communication scheme used with other peripheral devices 16. As such, the close proximity peripheral devices 16 can provide a low cost means for controlling devices, which are in close proximity to the automation controller 12. For example, in many cases, the automation controller 12 will be placed in close proximity to audio, video, and computer equipment, as well as lighting, which can be controlled via the low cost proximate peripheral devices 16.

FIG. 8a shows peripheral device 16 embodiments, in which a plurality of peripheral devices 16 form a control group, which share a common communication interface (transmitters, receivers, etc.) to the controllers 12 and/or 14. The sharing of the communication interface, and in some instances, some or all of the processing capability, provides for lower cost peripheral devices 16. In various embodiments, each of the individual peripheral devices $16_{1-n}$ in the control group is identified as a separate peripheral device 16.

Whereas, in other embodiments, the entire device 16 is identified as one peripheral device 16 with sub-devices $16_{1-n}$. The identification of the peripheral devices 16 as individual devices or sub-devices is generally left to the skilled artisan. When using sub-device identification, instructions can be given to the device as a whole, which can be left to the device itself to implement. For example, peripheral device 16 can be instructed to turn off, which causes the peripheral device 16 to turn off sub-devices $16_{1-n}$. In the individual device implementation, instructions to turn off are sent to each of the devices $16_{1-n}$ for action.

The FIG. 8a embodiment, which is shown as a plug strip, is purely for exemplary purposes, as the common interface/processing architecture can be implemented for any application in which the devices are in relatively close proximity or can communicate effectively. For example, track lighting, holiday decorations, etc. can be implemented using this structure.

As shown in FIG. 8b, the peripheral devices 16 also can be configured to communicate with other secondary devices 18 or systems. For example, the peripheral device 16 can include communication capability with a computer via USB, Ethernet, serial or parallel port or other connection, which can be wired or wireless. In these embodiments, the peripheral device 16 could send a system message to one or more secondary devices, such as a computer, that power was going to be interrupted and for the computer to perform a graceful shutdown. It could also send a signal that initiates the booting, or starting, up of the computer.

In various embodiments, the peripheral device 16 is embodied as a plug strip including a power cord for plugging into a power source, such as a standard electrical receptacle, and a plurality of electrical receptacles controlled at least in part by a common processor and using a common transmitter and receiver to communicate with the automation controller 12 via a first signal type, such as Zigbee, Zwave, PLC, 802.x, etc., and a computer via a secondary signal type, USB, etc., to send power up and power down signals to the computer. The common processor could be used to control all functions associated with the plurality of electrical receptacles or additional processors could be used with one or more of the receptacles.

The peripheral device 16 could further include an energy storage device, i.e., battery, which can be configured to retain sufficient energy to power 1) the peripheral device 16 to signal the computer or other secondary device 18 and 2) the computer or other device for a sufficient period to allow a graceful shutdown, in the event of a primary power failure to the computer or other secondary device 18. One of ordinary skill will appreciate that many computer and peripheral equipment types include APIs and other signaling protocols that enable the shutdown, restart, and turn-up of the equipment.

FIG. 9a shows other embodiments of peripheral devices 16 of the present invention. In these embodiments, one or more peripheral devices 16 are located outside of the operational range (shown as a dashed line) of the automation controller 12 and/or the remote controller 14, such as devices $16_{2-n}$ in FIG. 9a, referred to as "outside devices". In these embodiment, the peripheral device $16_1$ is configured to receive and transmit information to and from the outside devices $16_{2-n}$.

The relationship between the outside devices and the automation controller 12 can be implemented in various fashions, such as individual devices or sub-devices as discussed with respect to FIG. 8a. The outside devices may or may not be visible from an automation controller 12 inventory perspective. In various embodiments, the outside devices are visible to the automation controller 12 and are mapped based on their nearest neighbors in a mesh network topology and the outside devices and at least one device within the range ("inside device") are configured as repeaters, so that instructions from the automation controller 12 can reach the outside devices. In other embodiments, the outside devices are associated with the inside device and may be considered as attributes of the inside device. In this scenario, a controller, 12 or 14, sends a command to the inside device associated with the outside devices, which is then implemented on the outside devices at the appropriate time by the inside device.

The means in which the information is provided to and from the outside devices 16 may or may not be the same as the means in which the information was provided from the controllers, 12 or 14, to the peripheral device $16_1$ in the range. For example, if the outside devices are electrically connected, then externally powered devices using power line communications between outside devices may be appropriate, while wireless communications may be used for communications between the controller 12 or 14 and the peripheral device $16_1$. In other applications, outside devices may have diverse functions, such as outside lighting, contact switches on gates and mailboxes, and sensors, it may be more easily implemented using battery powered devices and the same wireless communications protocol as used in within the range of the automation controller 12. In still other embodiments, wireless communication can be provided by the automation controller 12 and the inside devices 16, whereas communication and power is provided to the outside devices via Ethernet.

FIG. 9b shows another embodiment of the present invention including a peripheral device $16_t$ that is configured to translate a message from the protocol used by the automation controller 12 to the protocol used by one or more secondary devices 18, which may be inside, shown as (a) in FIG. 9b, or outside (b) the coverage range of the automation controller 12. The translation can be between wireless protocols and/or wireline protocols and implemented in a variety of ways, such as mapping the signal from one protocol to another or by embedded one protocol signal within the other protocol signal, similar to a digital wrapper. For example, the peripheral device $16_t$ could translate a Zigbee protocol signal to an RS-485 signal to communicate with components in an HVAC system. The RS-485 link could be implemented as a full duplex, 4 wire solution or half-duplex 2 wire solution depending upon conditions, e.g., multiple radio interference conditions, and the amount and frequency of information being communicated through the link. In addition, two translator peripheral devices $16_t$ could be used to set up a link (c) using a different protocol, while still communicating with other devices using the protocol of the automation controller 12. In this implementation, this translator devices $16_t$ may be used to convert from wireless to wired protocols (in this example Zigbee and RS-485) to enable the signal to reach an area more easily accessed using a wired protocol, but where the signal may be sent wirelessly within the area. In this example, the translator device $16_t$ may be operated in a mode where the Zigbee message is inserted untouched into an RS-485 stream, which is sent to a second translator device $16_t$, where it is received. The 485 stream is analyzed and a Zigbee message is recreated by the second translator device $16_t$ and sent to the destination peripheral device 16.

In various embodiments, such as those shown in FIG. 4, the remote controller 14 could be used as a translator device to control one or more secondary devices 18. It will be appreciated that if a remote controller 14 is employed as a translator, it will have to be positioned properly to enable it to communicate with the secondary devices 18.

One of ordinary skill in the art will appreciate further that the range of an automation controller 12 can also be extended via repeater peripheral devices 16, which are used to amplify, typically be receiving and retransmitting signals, without altering the signals. Range extenders are known in the art and commonly available in 802.11 architectures. Of course, the repeater functionality can be embedded in other peripheral devices 16 to eliminate the expense of deploying stand-alone repeater devices.

Figure 10A:
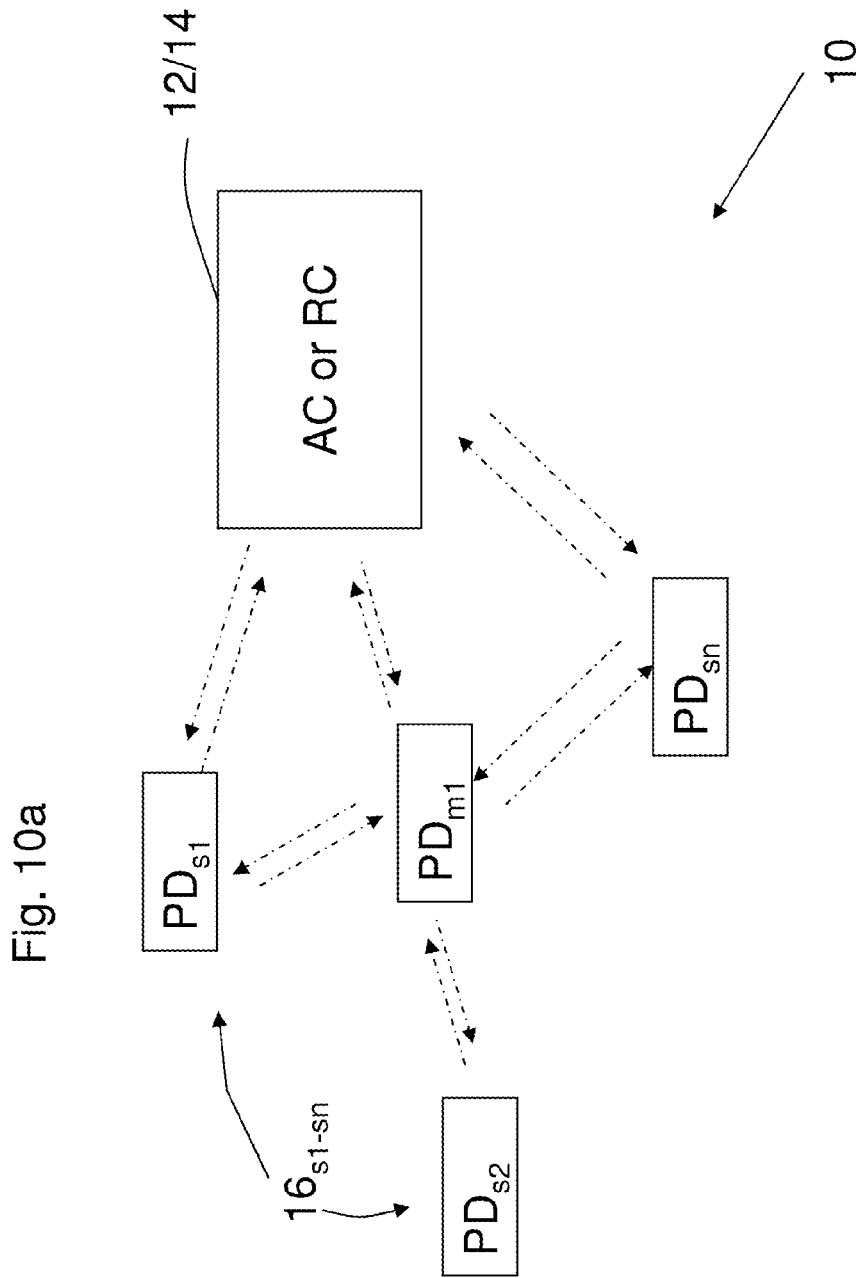

FIG. 10a shows embodiments of the system 10 including mobile peripheral devices $16^m$, which can be implemented to provide additional functionality to the system 10. Peripheral devices 16 that are fixed in space for a particular application can be referred to as stationary peripheral devices 16 to facilitate description. However, whether a peripheral device 16 is considered stationary or mobile may, in fact, depend upon the specific application and/or system configuration implemented by the user.

In the present invention, the mobile device $16^m$ can be used for determining when a subject (person, pet, object, etc) leaves or enters a structure or zone. In these embodiments, a peripheral device 16 can be attached, via bracelet, anklet, collar, or otherwise, to the subject and its transmission can be used to determine when the subject has left the zone, passes through a reception area or proximate to another device, etc. Mobile peripheral devices $16^m$ can be applied to home, office, or construction areas for theft protection and safety measures as well.

The system can be configured to geolocate the mobile peripheral devices 16''' operating in an environment with two or more other peripheral devices 16. For example, the received signal strength from various receivers can be used to locate the device by determining vectors for triangulation. This application allows a system to determine, not only when a subject has left a zone, but also, with some accuracy, where the transmitting device attached to the subject is located within the zone. This level of geo-location could be either constantly updated, or determined by querying the receivers in the zone. It will be appreciated that the system will determine the general location of the mobile device within the range of the system 10. The precision of the mobile device location will depend upon the desired amount and precision of the information received by the controller 12 from various stationary peripheral devices 16.

The frequency at which the system 10 tracks the mobile peripheral devices 16 can be configured by the user depending upon a desired implementation of the devices. For example, it may be desirable for the mobile peripheral devices 16 to transmit a signal, when it is prompted manually by remote controller 14 and/or automation controller 12. In these scenarios, the user may want only want to know the location when they are looking for the object, such as a remote controller 14, car keys, or even a pet. The automation controller 12 can be configured to request signals from the mobile peripheral devices 16''' at different intervals depending upon the location of the mobile peripheral devices 16''' within the system range.

In other instances, the user may want to know as soon as possible, or practical, that a child or disabled adult has left the range of the system 10. In these instances, the frequency and extent of the transmission must be balanced against the battery life of the device. In various embodiments, the mobile peripheral devices 16 will be driven by kinetic energy. An energy storage device, such as a rechargeable battery or capacitors can be provided to store excess kinetic energy. The kinetic energy driven device 16 has the benefit in that the energy to transmit signals is being generated by the motion of the object to which the mobile device 16''' is attached, which is precisely when the energy is needed for transmission. When the object is at rest and no kinetic energy is being generated, the transmission frequency can be much less, because the object is stationary and its location is presumably known.

In still other embodiments, the mobile device 16''' can lay dormant, i.e., not transmit a signal on its own, unless it is requested by an automation controller 12 or remote controller 14, or is activated/triggered by, or activates, another device in the system. For example, the mobile device 16''' could include an electromagnetic wave (e.g., RF, IR, etc.) detector and/or emitter/tag. In the case of a detector, when the device comes within the range of an emitter, which can be located proximate the exit of buildings, premises, room, or otherwise, the mobile device 16''' would be activated by the emitter signal from the emitter and begin transmitting signals to identify its location. If the mobile device 16''' includes an RF emitter, a RF detector located near a threshold of interest could be used to send a signal to the automation controller 12 that it has detected a mobile device emitter, at which time the automation controller 12 can ping the mobile device 16''' to send a tracking, or location, signal and/or other information that can be used by the controller to track the mobile device 16$^w$.

In various embodiments, such as those involving disabled adults and children, the mobile device 16''' will be regularly polled by the automation controller 12 and will be activated by, or activate, another device that is used to monitor the movement of the individual near thresholds of interest, building exits, etc. In this manner, regular updates will be obtained when a person is within a known area and the frequency of updates can be accelerated and notifications made, when a person leaves an area. It will be appreciated that the mobile device 16''' can perform a number of functions, such as measuring temperature, shock, pulse, etc. (i.e., health parameters) for individuals, in addition, to providing a tracking signal.

In application, when the automation controller 12 determines that an object being tracked with a mobile device 16''' has left some predefined area, such as exiting a building, the automation controller 12 can be configured to communicate the information to the user by the available means, such as email, text message, phone call, audible signal, etc. or merely log the time that object left the predefined range. The automation controller 12 could take the same or a different action when the object wearing the mobile device reenters the predefined range. An example of the automation controller 12 merely logging information could be logging when object that normally are expected to exit and reenter a range are being tracked, such as vehicles at a dealership or personnel at an office during normal business hours. Extending these same examples, the user may want to be notified when these objects enter and exit the premise during non-normal business hours.

Peripheral devices 16 can be deployed in data collection modes, if sufficient memory is provided for data storage during the collection interval, instead of transmitting the data as it is collected. The device 16 would then transmit the data collected over the interval to the controller or a display. For example, various sensors can be deployed that log data for periodic review and/or transmission, in lieu of regularly transmitting the data or waiting for a request by a controller.

A device 16 also may collect data on a fixed interval, but only transmit data when a threshold has been exceeded, such as high/low temperature, shock, gas concentration, humidity, etc., or upon request. Alternatively, the peripheral device 16 can perform some processing of the raw data and transmit only the processed data, while perhaps retaining the raw data for a period of time to allow for retrieval if necessary. For example, the peripheral devices 16 could process the raw data and transmit a moving average of the data and any extreme outliers to the data. In this manner, communication traffic in the system 10 is reduced.

As shown in FIG. 10b, devices 16 that are configured to collect data for later access also can be deployed in embodiments, in which two systems 10, or sub-systems of a larger system, are employed having non-overlapping ranges including geographically diverse configurations. For example, a device 16 that includes one or more sensors for detecting relevant conditions can be provided on the inside and/or outside of a shipping container. The data on the device 16 can be read before shipment by a system 10 at the point of origin and by a counterpart system 10 at the destination to determine the conditions to which the contents of the shipping container were exposed. It may also be possible to read the data en route. If the device 16 is provided within a sealed container, the data collected can be used to verify that a container was not exposed to conditions, temperature, humidity, shock, etc., that could damage the contents and the point in time and duration of the exposure to extreme conditions. The number of devices 16 deployed within a container and the sensors or other instruments included in or associated with the device 16 will generally depend upon the size of the container, (e.g., letter size package, cargo ship container) and the desire for redundant data collection, which may depend upon the value of the contents of the container. In practice, the carrier can be present and confirm the origin and destination data and the shipper/user can implement sufficient security, such that the device 16 is not reset or data compromised during shipment.

From a tracking perspective, the devices 16 used for shipping can be treated statically or as a mobile device 16''' by the system 10. For example, the shipping devices can be detected before or after the device enters a facility to provide data on whether shipments should be rejected, inspected, and/or accepted from a carrier. In other embodiments, each of the geographically diverse systems 10 can be included in a broader overall system from a network management level, such that peripheral devices 16 in each of the local systems can be registered and status maintained in an overall database, such that when the peripheral device 16 re-enters the coverage area of one of the system 10, it can be detected and the data logged. The overall database could be enabled in various configurations by one of ordinary skill. For example, the overall database for the plurality of systems, or automation controllers 12, could be embodied in a multi-level automation controller architecture, in which a master controller provides at least some control over multiple automation controllers 12 or the overall database may be merely a shared database that is accessible by multiple systems.

In various embodiments, the system 10 includes a limited purpose remote controller ("LPRC") 22, which can be a wall mounted, free-standing, or handheld device. The LPRC 22 can be embodied as a configurable on-off or dimmer switch that can be used to control one or more peripheral devices 16 directly and/or via the automation controller 12 or the remote controller 14. For example, the LPRC 22 can be configured to control one light or one electrical receptacle in a room similar to a traditional light switch. Alternatively, the LPRC 22 could be configured to control a group of lights and/or other peripheral devices 16. For example, the LPRC 22 could be mounted as a wall switch that could control all of the lights in a basement, turn on and off all of the components in an entertainment system, etc., even if those lights and components are on different wiring circuits.

FIGS. 11-16 depict various embodiments of the LPRC 22, which for exemplary purposes, is described in terms of on-off, toggle, or dimmer wall switch. Instead of opening and closing a circuit as in a traditional light switch, the LRPC 22 requests the controller to issue a command to function device to perform a function, such as to turn on or off one or more switches and/or receptacles. In an embodiment, flipping the switch (FIG. 11) one direction cause one or more lights controlled by function devices to be turned on and flipping the switch in the other direction causes the same lights to turn off. For a button (FIG. 12), the on-off instructions alternate with each push. In other embodiments, the LPRC could be activated using access control or presence technology, such as RFID or by placing a card in slot or reader.

In this manner, a wall switch could be used to control any and/or all of the outlets/lights, etc. in a room, rooms, or building, not just those hardwired to a wall switch during construction. The switch can be viewed as a limited purpose remote control for interfacing with the controller and/or peripheral devices 16 via a limited interface.

Additional functionality can be provided on the LPRC 22. For example, multiple switches can be packaged similar to traditional circuit control switch, A/B type slide switches can be added to the traditional flip switches to allow the switch to toggle additional functions (FIGS. 3 and 4). The multi-function switches can employ common or separate processors, transmitters, or receivers depending upon the desired level of functionality (FIGS. 5 &6). The switch can be powered via battery or external power. The function of the switch can be programmed, most likely via the controller, to perform the desired function upon actuation of the LPRC.

In various embodiments, the LPRC 22 can be configured to send a generic automation instruction to an automation controller 12 or a remote controller 14. Upon receiving the generic instruction, the controller will execute a reconfigurable instruction set controlling a group of one or more peripheral devices 16. In some embodiments, the same instruction may be sent whenever the LPRC 22 is actuated. In these embodiments, the controller will receive the instruction from the LPRC 22 and execute an instruction sequence for controlling one or more peripheral devices 16 tied to the receipt of the LPRC 22 instruction. For example, the first signal received from the LPRC 22 might cause the automation controller 12 to turn on one or more lights. The next three signals received from the LPRC 22 in this example, might cause the might cause the automation controller 12 to turn the lights to 66%, 33% and 0% (off) power, respectively.

In other embodiments, the LPRC 22 will send the actual automation instructions, either directly or via a controller, that instruct the peripheral devices 16 to perform the automation function. In these embodiments, the automation controller 12, and perhaps the remote controller 14, can be used to program the LPRC 22 to send automation instructions for a group of one or more peripheral devices 16. In yet other embodiments, the LPRC 22 will send different generic instructions depending upon its actuation, such as flipping a switch up and down. The controller could be configured to execute different automation commands for each generic instruction received from the LPRC 22.

As described above, the system 12 can be deployed in a vast number of configurations to achieve the functionality and cost objective of the end user. The automated monitor and control aspects of the system 10 also enable it to provide higher level functions, such as security and energy management.

In various embodiments, the automation system will perform integrated energy management of part or all of a facility. For example, a user in a may establish a multi-level energy management structure. At a first level, the system administrator establishes administrator settings for day and time of day settings for the HVAC system, hot water heater, etc. Typically, this will involve setting a first temperature range for hours of operation and a second temperature range non-operational hours. Various settings for lighting in the facility may also be established.

A second level of control can be implemented by monitoring usage at the circuit level for an area, as well as for confirming the integrity of overall and individual usage data. Circuit monitoring also provide the user with data for planning peripheral device roll out, as well as for providing more granular operational hour control.

A third level of control may be implemented at the work space and common area level. For example, the temperature of a work space may be controlled depending upon whether or not a person is present at the facility or whether a meeting is scheduled or people are present in a work space, such as a conference room. Also, the hallways and other common areas may be controlled to a different temperature and/or lighting intensity. Circuit level control also can be used in some just in time power deployments, when the first and last person enters a work area and for spaces and/or jobs that are not suitable for control at the individual work space level.

The concept of controlling the temperature and lighting depending upon the presence of a person at the home or work place can be extended more generally to "just in time" energy management. In various embodiments, the automation controller 12 provides access control and/or monitoring or interacts with an access control/monitor system and part of a person's work space or a residence is not supplied electricity unless the person is present.

Upon detection of a person entering a facility, the automation controller 12 would turn on the supply of power to a person's work space and adjust the temperature of the work space accordingly. In various embodiments, the automation controller 12 could begin powering up computer equipment and peripherals, so the equipment is ready to use when a person reaches their work space. When a person leaves a work space, the automation can direct the return of the work space to non-operational or out-of-the-work-space operational set points. An analogous procedure can be implemented for a residence.

At another level, the automation controller 12 can coordinate the different energy management activities within a facility and/or work space. For example, a work space environment will be defined at least in part by the temperature and lighting intensity. The automation controller 12 can be configured to balance the solar impact, i.e., light and heat provided by sunlight or natural light, within an area with the light and heating/cooling provided by the building systems to minimize the energy cost.

In this case, the automation controller 12 could control various peripheral devices 16, including lights, HVAC vents, window blinds, etc. in a coordinated manner to reduce energy consumption. For example, the temperature and light intensity within a work space/area is defined in the controller 12. During the course of the day, the blinds would be open to varying degrees. When it is night, the controller 12 can close all of the blinds for privacy and to increase its effectiveness as a thermal barrier. During the day time, but not during operational hours, the controller 12 can leave the blinds closed, if desired, or open the blinds an appropriate amount to balance the solar impact with the temperature and lighting demands of the space. During non-operational daylight hours or when the work space is unoccupied, the control of natural light does not have to consider glare from natural light when determining the amount of natural light to allow in the space or the direct impingement of sun light on a person in the space. Whereas, when a person is present in the work space, solar impact issues typically have to be considered.

The specific types and number of peripheral devices 16 used to coordinate the light and temperature control provided by the facility/building system with the solar impact, sun light and thermal energy, can be determined by the skill artisan. For example, one or more light controllers and temperature controllers for the building systems can be deployed in the area along with blind controllers, external and internal temperature and light sensors, motion detectors, etc. The automation controller 12 can be configured to maintain administrator settings for light intensity and temperature in the area by operating the blind controller to allow sun light and thermal energy to enter the area and adjusting the light and temperature controllers to control the amount of lighting and energy provided by the building systems accordingly. The operation of the devices 16 can be configured in various ways, but a default configuration may be to minimize lighting and HVAC costs for the area, while operating in conformance with the area settings.

The automation controller 12 also could interact with an area controller 13 that could be coordinating the peripheral devices 16 within an area. For example, the area controller could include or be associated with various sensors, such as temperature, light intensity, and motion, in the area, which provide local information used to control the area environment. The area controller could be used merely to provide a single point of contact for a given area to the automation controller 12 or could be configured to control various actions of the peripheral devices 16 in the area. In various embodiments, the area controller can be used to turn power on and off to an area, which can be triggered manually, flipping a switch, inserting a card, etc. or upon detection of a person, via RFID or otherwise, or condition, similar to an LPRC as discussed above.

In various embodiments, the automation controller 10 overseeing the area controllers, or the area controllers themselves, signal a circuit interrupt peripheral device 16 that can be used to open a circuit passing through an area. The circuit interrupt device can be included in another peripheral device, such as a controlled outlet or light switch. The circuit interrupt device can be implemented at various points in the circuit to enable bulk control of multiple outlets and/or switches, thereby enabling large amounts of the building electrical system to be controlled without significantly increasing the cost.

As greater control of the electrical system is implemented, automation controllers can be configured to send out various types of information to peripheral devices and electrical components. For example, the automation controller 12 and/or area controller can send information, such as the time and day, to devices that were connected to outlets, etc. that were powered down, as the devices are turned back up. The information can be sent to each specific device using its identification.

Alternatively, a broadcast command can be sent by one of the controllers (automation, area, remote) that can be interpreted by a class of peripheral devices and/or enabled electrical appliances/components. For example, an electrical component including a time keeping device, such as a clock, a microwave, a coffee maker, a washer/dryer, etc. could be configured to receive a standard protocol signal to provide the time and/or date. Other types of instructions could be analogously sent out, such as a broadcast temperature setting change to multiple thermostats.

Similar functionality can also be enabled in the peripheral devices 16. For example, one or more of the controllers can send a broadcast command or information, such as time/day, which may initiate various responses when received by the peripheral devices 16 depending upon the programming of the devices 16. For example, if a facility is supposed to be placed in a given state on a given date and time, the automation controller 12 may be required to issue numerous commands to place the various peripheral devices 16 in their proper state. An alternative to issuing device specific commands is to send a broadcast message, such as the time, day, new operating state, etc. in the general protocol. Peripheral devices 16 can recognize that message from that controller and act according to an established action. Returning to the facility example, the automation controller 12 could send a message, "Monday, $1^{st}$ shift", and peripheral devices 16 configured to respond to that message from that controller would assume the proper state for that period.

For energy management, the system 10 generally will be implemented by an administrator that configures the automation controller 12 and add peripheral devices 16 to the system. The administrator will generally establish various settings ("administrator settings") for the performance of functions relating to energy consumption for the peripheral devices 16 based on the day, time of day, the presence of at least one person within an area in the facility, environmental conditions outside the facility and solar impact within the area.

The administrator settings can include set points, limits, and ranges, and provide for user input consistent with the administrator settings. In various embodiments, the automation controller 12 can be configured to determine the financial impact of allowing user variations to the administrator settings. The information can be used to modify the administrator settings and suggest alternative user settings.

The system can be configured to adapt to the behavior of personnel with the facility, which can modify administrator settings or merely provide the data to the administrator for information or action. For example, the system can monitor the presence of personnel in the area and adapt the set point times for transitioning from a person present in the area settings to not present in the area settings.

The transition set point times can be different for different energy consuming devices in the area. For example, various equipment lights and displays can be dimmed or turned off almost immediately when a person leaves the area, while it is often not desirable to turn off or hibernate a computer immediately when a person leaves the area. Voice over Internet Protocol (VoIP) phones, which do not locally host messaging or other services, can be turned off when a person is not present in the area and/or facility. Also, displays can be turned off when not in use and turned on when the server forwards a call to the phone or the phone is prompted by the user.

Other devices that employ Power over Ethernet ("PoE") can also be turned on and off via the system 10, as well as part or all of the local area network ("LAN"), when there are no users on the LAN. In various embodiments, the devices 16 can be configured to transmit a wake up, or start up, signal back to the LAN equipment, i.e., servers, switches, etc., to power up a portion of the LAN for use. In various embodiments, the devices 16 can be implemented to communicate with secondary devices, such as those embodied in and described relative to FIGS. 8a&b, and with the LAN server. In these embodiments, the device 16 can communicate start up and/or shutdown signals to both the LAN equipment and the computer equipment. An example of these embodiments a is a plug strip/surge protector that is connected via Ethernet cables to a computer and the LAN. In the case of a start-up, upon notification that a user of the computer is present in the facility or otherwise, the device 16 will send start-up signals to both the computer and the LAN. The device 16 will also enable the supply of power to the power receptacles in the plug strip allow the computer and other electrical devices to power up. Similarly, when there is to be a shut down, because the user is no longer present, there is a power interruption, or otherwise, the device 16 would send shut down signals to the computer and the LAN.

Various access control technologies, such as RFID, IR, etc. can be used to track the movement of personnel and assets within a facility, in addition to access to the facility. Access tracking within the facility can be used to trigger the transition from a person being present in an area to not present, and vice versa. For example, the access control system can detect when a person moves between the different parts of a facility, such as laboratory, manufacturing, administrative, etc., and transition the person's work area to present or not present state.

The extent of deployment of the system 10 will determine the level of detail of the information provided to the user and available for control of the information. In various embodiments, the system 10 will include at least one peripheral device 16, such as a current, power, and/or voltage monitor, for monitoring the overall energy consumed within a managed area as a function of time. The various peripheral devices 16 deployed within the managed area will provide more specific electrical usage data. In a typical scenario where the peripheral devices 16 are not monitoring all electrical consumption points, the system 10 can be configured to provide overall, circuit, monitored, and unmonitored usage statistics that will allow a user to determine the cost effectiveness of additional monitoring in the managed area.

The system 10 can be configured in many different ways depending upon the extent of the deployment within a facility and the objectives. The system 10 can provide detailed reporting and analysis of energy usage and the operation of the various monitored equipment. The operational information can be used in combination with electricity rates from the utility to align the usage of electricity with the cost of electricity. For example, the controller 12 can implement rules to allow some activities only at night during hours of lower cost electricity. Also, the user can analyze the impact of replacing equipment with new equipment, installing solar or other power generation capabilities on site, or employing other sources of energy during various times of the day.

The system 10 can also be configured to participate in demand-response programs in cooperation with utilities and/or energy brokers, in which during times of peak demand, the operational set points of one or more energy consuming devices, typically the air conditioning unit, is varied to reduce power consumption during period of high demand. Using the system 10 of the present invention, the demand-response program can be implemented at a more specific level to provide additional savings and improved comfort. For example, instead of the utility or energy broker cycling the air conditioning units for a facility, the automation controller 12 could increase the temperature set point for various parts of the building that are less sensitive to temperature change or have a local, non-utility power capability, such as batteries, solar, etc., which could pick up the load. The controller 12 can also delay certain processes from occurring until the demand-response condition has passed.

In various embodiments, the actual energy consuming devices that are operated to consume less energy can be tailored to the amount of energy reduction being requested by demand-response client, i.e., utility or energy broker. For example, the automation controller 12 may determine that the requested energy consumption reduction requested by the client could be achieved by raising the temperature in various parts of the facility, such as rooms not currently occupied, by a few degrees and dimming the lighting in the hallways, rather than cycling the air conditioning for the entire facility.

In application, the administrator of the system can assigned various peripheral devices 16 associated with energy consuming devices to be turned off or operated at lower power settings as a function of the requested power reduction. The administrator can also establish a hierarchy of devices and the associated energy reduction for each device, such that the system 10 starts at the top of the list and implements the reduced energy settings until the cumulative reduction of all the devices achieves the requested reduction.

In various applications, the administrator can establish target energy reduction amounts based on the demand-response system. For example, a demand-response system can be established by the client that provides for varying levels of incentives, e.g., rebates, credits, points, etc., corresponding to the extent of the energy reduction made by the user. These types of demand-response system enable the administrator of the system 10 to reduce energy consumption according to the established hierarchy in order to achieve a target incentive amount established by the client as a function of the energy reduction.

As previously described, the system 10 can be grouped into various topologies depending upon the number of devices, geographic scope, and desired performance of the different parts of the system 10. An approach to dissecting large networks of devices to avoid bandwidth and latency problems is to break the system 10 into a number of small networks, i.e., sub-networks, and then implement a "network of networks" management approach using a higher level system to view the collection of networks as a single network from an energy management perspective as depicted in FIG. 17.

In various network embodiments, limited "tunneling" or routing of only selected building management and energy efficiency information to/from the higher level system is performed, while also maintaining the local control of the sub-network. The local network controller, or area controller as described above, routes energy control and usage information to the higher level system for the peripheral devices it manages, and also routes information and requests from the higher level system to the local peripheral devices 16.

Figure 17:
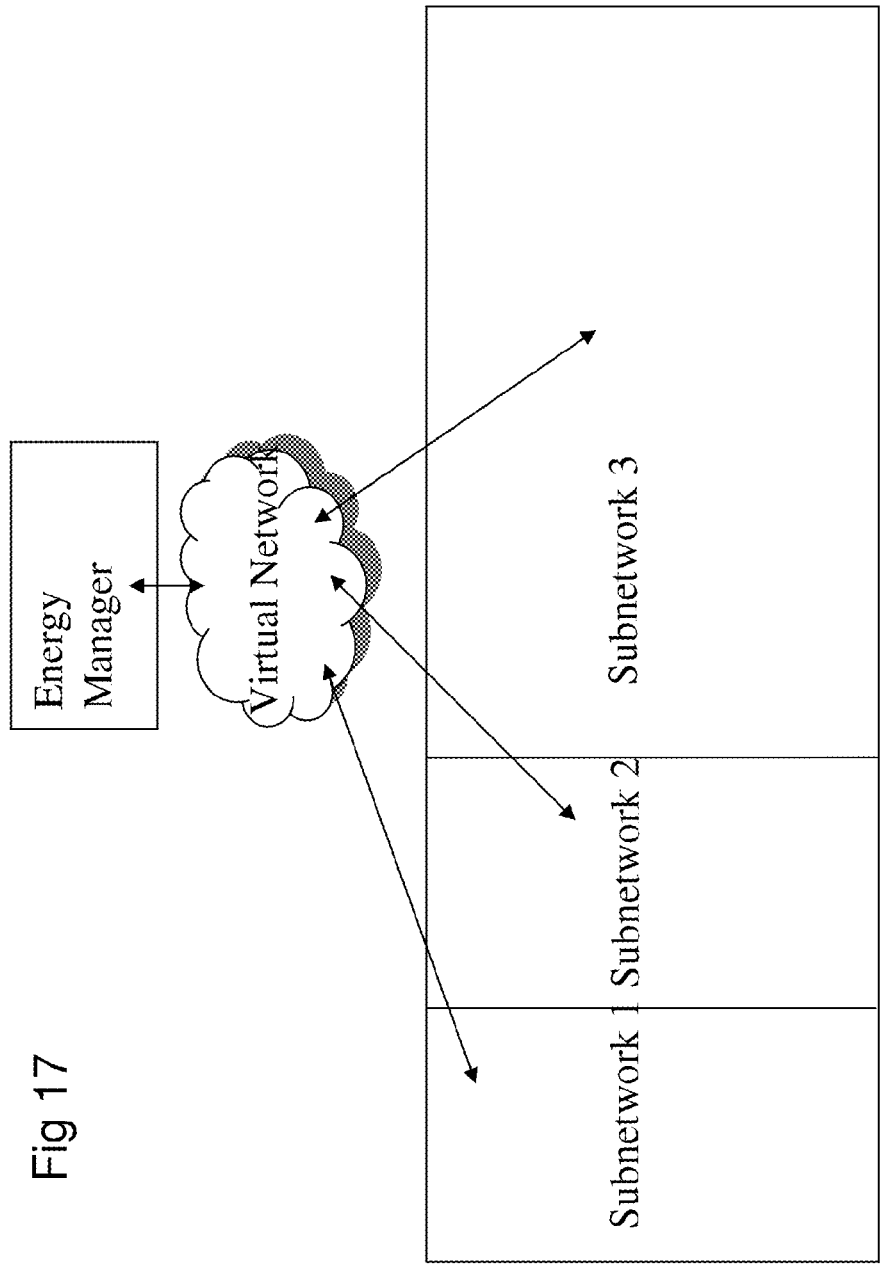
FIG. 17 shows embodiments of network architectures of the present invention.

FIG. 17 shows a virtual energy management network that is created by the collection of subnetworks of building control and monitoring devices. The subnetworks would route energy efficiency information and control functions between the controlling energy efficiency and/or demand response device and the remote peripheral devices contained within each subnetwork. Additionally, this approach is unique in that the energy efficiency device can control energy devices at the boundary of each subnetwork to affect energy consumption across the entire structure, instead of treating each subnetwork as a compartmentalized energy zone.

As the size of the automation system 10 increases, the task of turn-up and maintenance becomes a corresponding more significant effort. As such, it becomes increasingly desirable to increase the flexibility and control of the system. However, it may be further desirable to implement the capability to enable various architectures in small system deployments, such that it can be scaled appropriately, if necessary.

Figure 18:
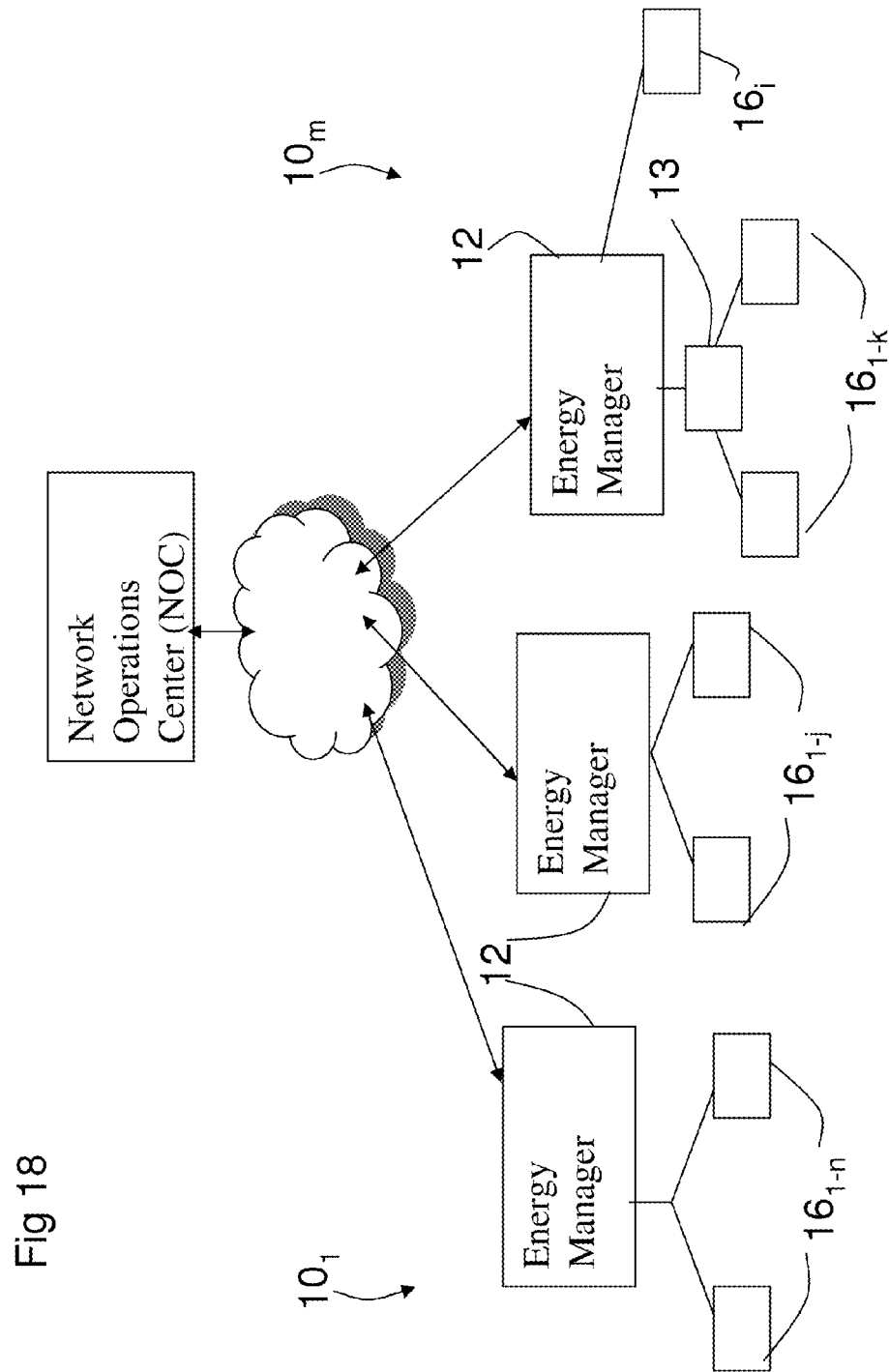
FIG. 18 shows embodiments of network architectures of the present invention.

In various embodiments of automation system 10, such as shown in FIGS. 5b, 10b, and 18, the automation controller 12, and in some instances, the remote controller 14 and/or various peripheral devices are configurable to implement a secure data link with an external network resource, such as provided in a remote network operation center ("NOC") 60 or other remote control device or system. The secure data link is used establish communication of operational information between the controller 12 and the NOC 60 to enable remote operation, administration, and management of the system 10. It will be appreciated that interaction with the system via the external network resource can be performed by various parties, such as network operations personnel, third party service providers, or the system owner. For example, the owner of the system can employ a network operations service provider to monitor and maintain the network and/or engage the external network resource provider to provide the owner with access through the secure data link to their system 10 via a web interface or otherwise.

It will be further appreciated that the NOC or other external network resource embodiments can include many different resources that are available to the system 10, including servers, data storage, remote and local user access interface, communication links to 3$^{rd}$ parties, such as utilities, demand-response clients, third party service providers, security and emergency personnel, etc.

The operational information can include a wide variety of information that might be useful to one of ordinary skill in the art operating or using the system 10 via an interface to the automation controller or from the NOC. For example, various measured and calculated data can be provided from the various controllers 12 to the external network resource. Operational notices including demand/response, curtailment, operational plan changes notices can be communicated in either direction. In addition, communication of information between automation controllers 12 can be facilitated through the external network resource, such as data pertaining to mobile peripheral device 16$^m$, as described with respect to FIG. 10b above.

The secure data link can be implemented using virtual private network ("VPN") software that runs on the controller 12 or other device. The secure data link is initiated by the controller 12 and not the NOC, so that network firewalls hosting the controllers 12 do not have to be exposed. In some instances it may be desirable to implement remote services employing sessions and links that are initiated by the external network resource. However, enabling outside initiated links presents an increased security risk, because a network port must be exposed, which is often times unacceptable for many automation applications, including energy management.

In various embodiments, the secured data link can be established upon device turn-up, so that configuration, registration, and turn-up can be remotely enabled, thereby reducing or eliminating the performance of these tasks by installation personnel. In addition, communication between the NOC and the various systems 10 deployed in a service area can be established by the secure data link on a periodic or continuous basis to enable the remote resources to provide services to the network. For example, the secure data link be used to collect usage data from and provide data to various systems 10. The secure data link could be used to issue notices to the various systems 10, such as a demand-response and curtailment notices. Also, it could be used to modify existing operational instructions, such as in the case of an unplanned change in operational state, e.g. school or business closing, program/meeting cancellation, extended travel, etc.

The establishment of a secure data link with external network resources provides some advantages, including enabling different roles based upon the common names used for authentication, the ability to establish a management plane on IP subnets distinct from a client management layer, the ability to manage all, or a subset of, appliances using established IP services such as multicast, SNMP, chat, etc., and decreasing or possibly eliminating the need for the end user to configure the system and perform system maintenance tasks, such as installing software updates, capturing error codes, etc.

The system 10 can include one or more VPN (Virtual Private Network) servers in the NOC together with the controllers 12, which can be referred to as network appliances in the VPN. The servers may or may not be centrally located, but each must be a member of the same VPN for any given system. Each network appliance can host VPN client software that is pre-configured with the necessary keys, certificates, server names, and server ports that are to be used when joining the private network. Since the VPN software tunnels network traffic, and all VPN connection attempts can be initiated by the network appliance, only dynamic/private network ports need to be used. Hence, there is no requirement for firewall configuration of the network to which the appliance is connected, which substantially improves the security of the system. This method also provides the appliance with the ability to avoid possible collisions between the appliance's local subnet IP address space and the VPN subnets' IP address space.

The Dynamic and/or Private Network Ports are those from 49152 through 65535, hexadecimal 0xC000 through 0xFFFF respectively (http://www.iana.org/assignments/port-numbers). This method uses ports 0xC000-0xCFFF to designate a class C private subnet, ports 0xD000-0xDFFF to designate a class B private subnet, and 0xE000-0xEFFF to designate a class A private subnet. The lower 12 bits of the port number are used to identify the subnet, thus the number of subnets per class can not exceed 4096.

The number of subnets and hosts per subnet that may be supported are contingent on the number of simultaneous VPN connections that each VPN server can support, as well as the size of the private address allocations as detailed in RFC 1918 (http://tools.ietf.org/html/rfc1918). The network mask for each network class can be chosen during the design phase. A benefit of this method is that both the VPN servers and VPN clients are able to identify an IP subnet based upon the port number.

The ports can be assigned such that each successive port number identifies the next subnet in that class. For example, given a 25 bit mask (255.255.255.128) the first class C private network would be 192.168.0.0/25, the next would be 192.168.0.128/25; the ports representing these would be 0xC000 and 0xC001 respectively. The port number increases until either the address space is exhausted or the port number reaches its maximum value. Ideally, a mask is chosen such that the number of available subnets does not exceed the port range, 0-4095. Using the class C, 25 bit mask example: the last subnet would be 192.168.255.128/25 and would be identified by port 0xC1FF.

Each VPN server can be configured to provide support for at least one VPN subnet. Multiple VPN servers may be networked together into a VPN server farm in order to scale the VPN to the desired size and to meet the desired performance characteristics.

Each networked appliance is configured such that the VPN client software has the ability to choose from at least one server and multiple ports. The VPN client software can be configured to run at startup and continuously retry connection attempts, as well as maintain the connection upon success. The VPN software determines the local IP subnet and dynamically excludes that subnet from the list of possible VPN subnet assignments. While it may be desirable to maintain a continuous secure data link, the system 10 can be configured to enable the link to be inactivated or terminated manually from either the external network resource side or the automation controller side of the link. In other embodiments, the secure data link is established periodically, as well as per a defined condition. For example, the automation controller 12 can be configured to establish a link or merely ping the external network after a defined period of time to serve as a heartbeat. Another connection condition can be set for when conditions change in the system 10 and the new conditions are reported to the external network resource.

In instances, where embodiments such as in FIGS. 10b and 18 include a plurality of automation controllers 12 that may be geographically diverse, it may be desirable for the external network resources to store data from the automation controllers 12 on other automation controllers 12. For example, local data analysis is possible by aggregating data from multiple automation controllers. This capability may be useful when it is not possible to maintain a data link with or otherwise get to the external network resource due to operational problems or operational data from many locations is being collected at a central facility for oversight and control operations. In these embodiments, it may be further desirable to enable the automation controller 12 at the central facility to establish various operating and reporting conditions and requirements that can be sent to the external network resources and multicast or otherwise communicated via the individual secure data link to the other automation controllers 12 in the system 10. One of ordinary skill will appreciate that various redundancy configurations are possible both for automation controllers 12 at the centralized facility or otherwise including, but not limited to, providing a redundant, or back-up, automation controller 12 are various facilities that is configured to assume control of the system 10 at the facility, if a primary or main automation controller 12 fails. The back-up automation controller 12 can establish its own secure data link with the external network resources that could maintain the backup controller in a state of readiness, but not operation unless needed.

These and other variations and modifications of the present invention are possible and contemplated, and it is intended that the foregoing specification and the following claims cover such modifications and variations.

What is claimed is:

1. An automation system comprising:
a plurality of peripheral devices, each configured to perform at least one function relating to energy consumption in a facility;
an automation controller in communication with the plurality of peripheral devices and providing for the control of the performance of the function by each device based on at least one input;
an external network resource configured to enable communication with the automation controller, wherein the automation controller is configured to establish a data link with the external network resource to enable the communication of at least operational information; and
at least one area controller configured to control at least one of the peripheral devices and be controlled by the automation controller, wherein the area controller is configured to communicate with the external network resource when the automation controller is unable to communicate with the external network resource.

2. The system of claim 1, wherein the automation controller and external network resource are configured to allow operational information from the automation controller and peripheral devices to be communicated to the external network resource.

3. The system of claim 1, wherein the automation controller and external network resource are configured to communicate operational notices including demand-response, curtailment and operational plan changes.

4. The system of claim 1, wherein the automation controller and external network resource are configured to enable system updates to at least one of the automation controller and the peripheral devices to be communicated and implemented by the automation controller.

5. The system of claim 1, wherein the external network resource is a virtual private network server remotely located from the automation controller and the data link is a secure data link established via the Internet using virtual private network software being executed on the automation controller.

6. The system of claim 5, wherein the automation controller is configured to establish the secure data link to the virtual private network server upon turn-up of the automation controller and maintain the secure data link unless manual inactivated.

7. The system of claim 5, wherein the virtual private network server is one of plurality of virtual private network servers that are configured to enable secure data links with at least one automation controller.

8. The system of claim 5, wherein at least one virtual private network server is configured to enable access to operational data communicated from the automation controller to the virtual private network server.

9. The system of claim 5, wherein at least one virtual private network server is configured to enable an owner of a plurality of automation controllers to access operational data communicated from the automation controllers.

10. The system of claim 5, wherein at least one virtual private network server is configured to enable an owner of a plurality of automation controllers to communicate operational information to the automation controllers from the virtual private network server.

11. The system of claim 5, wherein at least one virtual private network server is configured to communicate with an owner of the automation controller when a specified condition occurs including a failure of one of the automation controller and one of the peripheral devices.

12. The system of claim 1, wherein the external network resource is configured to store operational settings from one automation controller on another automation controller having a common owner.

13. A method of managing an automation system comprising:
   providing at least one virtual private network server;
   implementing an automation system including at least an automation controller configured to control a plurality of peripheral devices, each configured to perform at least one function relating to automation in a facility;
   configuring the automation controller to establish a virtual private network with the virtual private network server;
   overseeing the operation of the automation system via the virtual private network server; and
   configuring the external network resource to store operational settings from one automation controller in one system on another automation controller in another system having a common owner, and communicate with at least one area controller when the automation controller is unable to communicate with the external network resource.

14. The method of claim 13, wherein configuring the automation controller includes configuring the automation controller to establish and maintain a secure data link with the virtual private network server unless manually inactivated.

15. The method of claim 13, wherein overseeing includes overseeing the operation and reconfiguring setting on at least one of the automation controller and the peripheral devices.

16. The method of claim 13, wherein overseeing includes overseeing the operation and transmitting event notices to the automation controller.

17. The method of claim 13, further comprising enabling an owner of a plurality of automation systems to access data collected by the virtual private network server for the plurality of automation systems.

18. An energy management system comprising:
   a plurality of peripheral devices, each configured to perform at least one function relating to energy consumption in a facility;
   an automation controller in communication with the plurality of peripheral devices and providing for the control of the performance of the function by each device based on at least one input; and,
   an external network resource including at least a virtual private network server and configured to enable communication with the automation controller, wherein the automation controller includes virtual private network software configured to establish and maintain a secure data link with the virtual private network server to enable control of the automation controller via the virtual private network server wherein the external network resource is configured to enable operational settings from the automation controller in the system to be stored on another automation controller in another system having a common owner, and communicate with at least one area controller when the automation controller is unable to communicate with the external network resource.

* * * * *